US008980255B2

(12) United States Patent
Perretti et al.

(10) Patent No.: US 8,980,255 B2
(45) Date of Patent: Mar. 17, 2015

(54) TREATMENT OF AUTOIMMUNE DISEASE BY MODULATING ANNEXIN-1 (LIPOCORTIN 1)

(75) Inventors: Mauro Perretti, London (GB); Fulvio D'Acquisto, London (GB); Roderick John Flower, London (GB)

(73) Assignee: Queen Mary & Westfield College, London (GB)

( * ) Notice: Subject to any disclaimer, the term of this patent is extended or adjusted under 35 U.S.C. 154(b) by 0 days.

(21) Appl. No.: 13/131,927

(22) PCT Filed: Dec. 2, 2009

(86) PCT No.: PCT/GB2009/002810
§ 371 (c)(1),
(2), (4) Date: Oct. 5, 2011

(87) PCT Pub. No.: WO2010/064012
PCT Pub. Date: Jun. 10, 2010

(65) Prior Publication Data
US 2012/0034209 A1    Feb. 9, 2012

(30) Foreign Application Priority Data

Dec. 2, 2008 (GB) .................... 0822011.3

(51) Int. Cl.
*A61K 39/395* (2006.01)
*C07K 16/18* (2006.01)
*A61K 39/00* (2006.01)

(52) U.S. Cl.
CPC ........... *C07K 16/18* (2013.01); *A61K 2039/505* (2013.01)
USPC ................... 424/130.1; 424/133.1; 424/154.1

(58) Field of Classification Search
None
See application file for complete search history.

(56) References Cited

U.S. PATENT DOCUMENTS

| | | | | |
|---|---|---|---|---|
| 5,051,364 | A | | 9/1991 | Isacke et al. |
| 5,565,338 | A | * | 10/1996 | Ishizaka ........................ 435/70.2 |
| 2005/0113297 | A1 | * | 5/2005 | Francois et al. ................ 514/12 |
| 2006/0024315 | A1 | | 2/2006 | Schnitzer et al. |

FOREIGN PATENT DOCUMENTS

| | | | |
|---|---|---|---|
| CN | 1726395 | A | 12/2013 |
| WO | 2005/027965 | A1 | 3/2003 |
| WO | 2003057715 | | 7/2003 |
| WO | 2005/117848 | A2 | 12/2005 |
| WO | 2010064012 | A2 | 6/2010 |

OTHER PUBLICATIONS

Yang et al Modulation of inflammation and response to dexamethasone by Annexin 1 in antigen-induced arthritis. Arthritis Rheum. Mar. 2004;50(3):976-84.*
Yang et al. Inhibitory effect of annexin I on synovial inflammation in rat adjuvant arthritis. Arthritis Rheum. Jul. 1999:42(7):1538-44.*
Yang et al. Antiinflammatory effect of lipocortin 1 in experimental arthritis. Inflammation. Dec. 1997;21(6):583-96.*
Iaccarino et al. Anti-annexins autoantibodies: Their role as biomarkers of autoimmune diseases. Autoimmunity Reviews 10 (2011) 553-558.*
Owens RJ, Young RJ. The genetic engineering of monoclonal antibodies. J Immunol Methods. 168(2):149-165, 1994.*
Huitinga et at., Effect of annexin-1 on experimental autoimmune encephalomyelitis (EAE) in the rat. Clin Exp. Immunol. 111:198-204.*
Swanborg et al. Clinical Immunology and Pathology, 77: 4-13, 1995.*
Dijikstra et al. TIPS Reviews, 14: 124-129, 1993.*
D'Acquisto F., From the bench to the pipeline: Testing the immunosuppressive potential of novel therapies targeting annexin A1. Immunology, (Dec. 2010) vol. 131, Supp. SUPPL. 1, pp. 159. Abstract No. 645.*
Tagoe et al. Annexin- Mediates TNF-α-stimulated Matrix Metalloproteinase Secretion from Rheumatoid Arthritis Synovial Fibroblasts. The Journal of Immunology. 181:2813-2820, 2008.*
Flower, R. J., et al., Lipocortin-1: cellular mechanisms and clinical relevance, Trends Pharmacol Sci. Mar. 1994;15 (3):71-6.
D'Acquisto, F., et al., Impaired T cell activation and increased Th2 lineage commitment in Annexin-1-deficient T cells, Eur J Immunol. Nov. 2007;37(11):3131-42.
D'Acquisto, F., et al., Annexin-1 modulates T-cell activation and differentiation, Blood. Feb. 1, 2007;109 (3):1095-102.
D'Acquisto, F., et al., Glucocorticoid treatment inhibits annexin-1 expression in rheumatoid arthritis CD4+ T cells, Rheumatology (Oxford). May 2008;47(5):636-9.
D'Acquisto, F., et al., Annexin-A1: a pivotal regulator of the innate and adaptive immune systems, Br J Pharmacol. Sep. 2008;155(2):152-69.
D'Acquisto, F., On the adaptive nature of annexin-A1, Curr Opin Pharmacol. Aug. 2009;9(4):521-8.
Huggins, A., et al., Annexin-1-deficient dendritic cells acquire a mature phenotype during differentiation, FASEB J. Apr. 2009;23(4):985-96.
Huitinga, I., et al., Effect of annexin-1 on experimental autoimmune encephalomyelitis (EAE) in the rat, Clin Exp Immunol. Jan. 1998;111(1):198-204.
Lim, L. H., et al., Promoting detachment of neutrophils adherent to murine postcapillary venules to control inflammation: effect of lipocortin 1, Proc Natl Acad Sci U S A. Nov. 24, 1998;95(24):14535-9.
Maderna, P., et al., Modulation of phagocytosis of apoptotic neutrophils by supernatant from dexamethasone-treated macrophages and annexin-derived peptide Ac(2-26), J Immunol. Mar. 15, 2005;174(6):3727-33.

(Continued)

*Primary Examiner* — Maher Haddad
(74) *Attorney, Agent, or Firm* — Pepper Hamilton LLP

(57) ABSTRACT

The present invention provides a specific binding molecule which binds to Annexin-1 (Anx-A1) for use in the treatment of T cell-mediated disease.

10 Claims, 23 Drawing Sheets

(56) References Cited

OTHER PUBLICATIONS

Paschalidis, N., et al., Modulation of experimental autoimmune encephalomyelitis by endogenous annexin A1, J Neuroinflamm. Nov. 13, 2009;6:33.

Pepinsky, R. B., et al., Monoclonal antibodies to lipocortin-1 as probes for biological function, FEBS Lett. Feb. 26, 1990;261(2):247-52.

Perretti, M., et al., Annexin A1 and glucocorticoids as effectors of the resolution of inflammation, Nat Rev Immunol. Jan. 2009;9(1):62-70.

Scannell, M., et al., Annexin-1 and peptide derivatives are released by apoptotic cells and stimulate phagocytosis of apoptotic neutrophils by macrophages, J Immunol. Apr. 1, 2007;178(7):4595-605.

Vong, L., et al., Annexin 1 cleavage in activated neutrophils: a pivotal role for proteinase 3, J Biol Chem. Oct. 12, 2007;282(41):29998-30004.

Jacobs, M. J., et al., Role of IL-2 and IL-4 in exacerbations of murine antigen-induced arthritis, Immunology. Nov. 1994;83(3):390-6.

Tagoe, C. E., et al, Annexin-1 mediates TNF-alpha-stimulated matrix metalloproteinase secretion from rheumatoid arthritis synovial fibroblasts, J Immunol. Aug. 15, 2008;181(4):2813-20.

Oliani, S. M., et al., Annexin 1 localisation in tissue eosinophils as detected by electron microscopy, Mediators Inflamm. Oct. 2002;11(5):287-92.

Buckingham et al., 'Lipocortin 1: a second messenger of glucocorticoid action in the hypothalamo-pituitary-adrenocortical axis'. Molecular Medicine Today, 1997, vol. 3, No. 7, 296-302.

Buckingham. 'Stress and the neuroendocrine-immune axis: the pivotal role of glucorticoids and lipocortin 1' British Journal of Pharmacology 1996, 1-19.

Cui et al., 'Overexpression of annexin a1 induced by terephthalic acid calculi in rat bladder cancer', Proteomics, 2007, vol. 7, No. 22, 4192-4202.

John et al., 'Annexin A1 and the formyl peptide receptor family: neuroendocrine and metabolic aspects', Current Opinion in Pharmacology, 2008, vol. 8, No. 6 765-776.

Liu et al., 'Identification of annexin A1 as a proinvasive and prognostic factor for lung adenocarcinoma', Clinical & Experimental Metastatis, 2011, vol. 28, No. 5, 413-425.

Solito et al., 'Annexin A1 in the brain-undiscovered roles?', Trends in Pharmacological Sciences, 2008, vol. 29, No. 3 135-142.

Cai et al., "Preparation and Identification of Monoclonal Antibody Against Annexin I", Tumor, 2006, 26 (11):979-983.

Non-final Office Action for related U.S. Appl. No. 13/702,593 dated Aug. 29, 2014.

Falini et al., "Simple diagnostic assay for hairy cell leukaemia by immunocytochemical detection of annexin A1 (ANXA1)", Lancet, Jun. 5, 2004;363(9423):1869-70.

Winkler, K. et al. "Changing the Antigen Binding specificity by Single Point Mutations of an Anti-p24 (HIV-1) Antibody", The Journal of Immunology, 2000, 165(8): 4505-4514.

Brown, M. et al., "Tolerance to single, but not multiple, amino acid replacements in antibody V-H CDR2: A means of minimizing B cell wastage from somatic hypermutation?", The Journal of Immunology, 1996, 156(9): 3285-3291.

Maynard, J.A. et al., "Protection against anthrax toxin by recombinant antibody fragments correlates with antigen affinity", Nature Biotechnology, 2002, 20(6): 597-601.

Barderas, R. et al., "Affinity maturation of antibodies assisted by in silico modeling", Proceedings of the National Academy of Sciences, 2008, 105(26):9029-9034.

O'Kennedy et al., "Antibody Engineering: an overview", Abstract, Essays Biochem, 1991, 26:59-75.

Official Action dated Nov. 12, 2014 in U.S. Appl. No. 13/702,593.

Vajdos et al., Comprehensive functional maps of the antigen-binding site of an anti-ErbB2 antibody obtained with shotgun scanning mutagenesis, J. Mol. Biol. (2002) 320(2):415-428.

Rudikoff et al., Single amino acid substitution altering antigen-binding specificity, Proc Natl Acad Sci USA (1982) 79 (6):1979-1983.

Paul, Fundamental Immunology, 3rd edition, 1993, 292-295.

* cited by examiner

Figure 1A
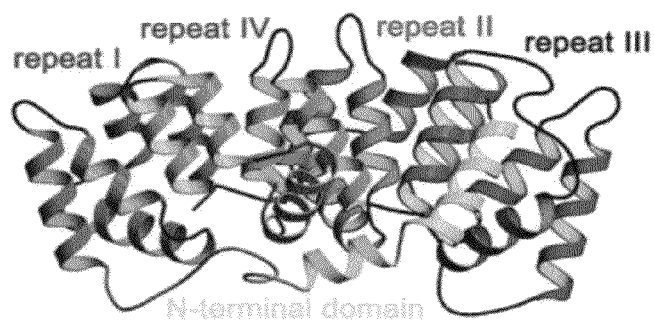
Figure 1B
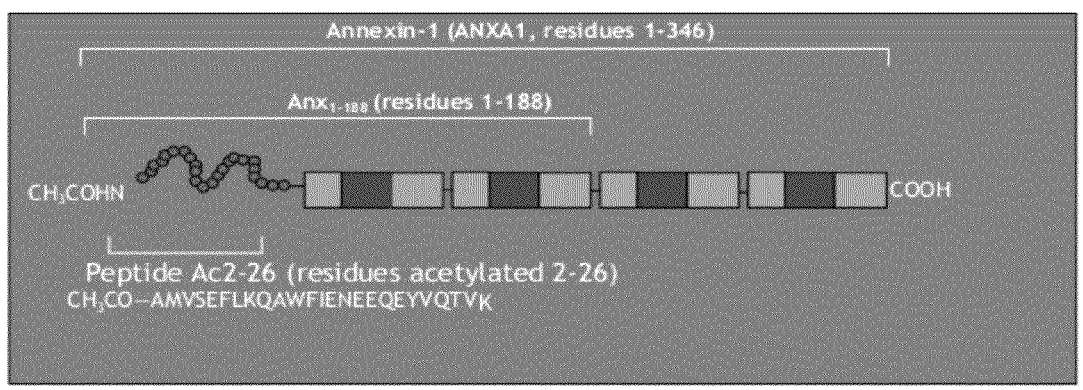
Figure 1C
CH$_3$CO-AMVSEFLKQAWFIENEEQEYVQTVK

Figure 2a (i)

```
  1    MAMVSEFLKQ  AWFIENEEQE  YVQTVKSSKG  GPGSAVSPYP
 41    TFNPSSDVAA  LHKAIMVKGV  DEATIIDILT  KRNNAQRQQI
 81    KAAYLQETGK  PLDETLKKAL  TGHLEEVVLA  LLKTPAQFDA
121    DELRAAMKGL  GTDEDTLIEI  LASRTNKEIR  DINRVYREEL
161    KRDLAKDITS  DTSGDFRNAL  LSLAKGDRSE  DFGVNEDLAD
201    SDARALYEAG  ERRKGTDVNV  FNTILTTRSY  PQLRRVFQKY
241    TKYSKHDMNK  VLDLELKGDI  EKCLTAIVKC  ATSKPAFFAE
281    KLHQAMKGVG  TRHKALIRIM  VSRSEIDMND  IKAFYQKMYG
321    ISLCQAILDE  TKGDYEKILV  ALCGGN
```

(ii)

```
   1    ATGGCAATGG  TATCAGAATT  CCTCAAGCAG  GCCTGGTTTA
  41    TTGAAAATGA  AGAGCAGGAA  TATGTTCAAA  CTGTGAAGTC
  81    ATCCAAAGGT  GGTCCCGGAT  CAGCGGTGAG  CCCCTATCCT
 121    ACCTTCAATC  CATCCTCGGA  TGTCGCTGCC  TTGCATAAGG
 161    CCATAATGGT  TAAAGGTGTG  GATGAAGCAA  CCATCATTGA
 201    CATTCTAACT  AAGCGAAACA  ATGCACAGCG  TCAACAGATC
 241    AAAGCAGCAT  ATCTCCAGGA  ACAGGAAAG   CCCCTGGATG
 281    AAACACTGAA  GAAAGCCCTT  ACAGGTCACC  TTGAGGAGGT
 321    TGTTTTGGCT  CTGCTAAAAA  CTCCAGCGCA  ATTTGATGCT
 361    GATGAACTTC  GTGCTGCCAT  GAAGGGCCTT  GGAACTGATG
 401    AAGATACTCT  AATTGAGATT  TTGGCATCAA  GAACTAACAA
 441    AGAAATCAGA  GACATTAACA  GGGTCTACAG  AGAGGAACTG
 481    AAGAGAGATC  TGGCCAAAGA  CATAACCTCA  GACACATCTG
 521    GAGATTTTCG  GAACGCTTTG  CTTTCTCTTG  CTAAGGGTGA
 561    CCGATCTGAG  GACTTTGGTG  TGAATGAAGA  CTTGGCTGAT
 601    TCAGATGCCA  GGGCCTTGTA  TGAAGCAGGA  GAAAGGAGAA
 641    AGGGGACAGA  CGTAAACGTG  TTCAATACCA  TCCTTACCAC
 681    CAGAAGCTAT  CCACAACTTC  GCAGAGTGTT  TCAGAAATAC
 721    ACCAAGTACA  GTAAGCATGA  CATGAACAAA  GTTCTGGACC
 761    TGGAGTTGAA  AGGTGACATT  GAGAAATGCC  TCACAGCTAT
 801    CGTGAAGTGC  GCCACAAGCA  AACCAGCTTT  CTTTGCAGAG
 841    AAGCTTCATC  AAGCCATGAA  AGGTGTTGGA  ACTCGCCATA
 881    AGGCATTGAT  CAGGATTATG  GTTTCCCGTT  CTGAAATTGA
 921    CATGAATGAT  ATCAAAGCAT  TCTATCAGAA  GATGTATGGT
 961    ATCTCCCTTT  GCCAAGCCAT  CCTGGATGAA  ACCAAAGGAG
1001    ATTATGAGAA  AATCCTGGTG  GCTCTTTGTG  GAGGAAACTA
1041    A
```

Figure 2b

```
1    MAMVSEFLKQ AWFIENEEQE YVQTVKSSKG GPGSAVSPYP
41   TFNPSSDVAA LHKAIMVKGV DEATIIDILT KRNNAQRQQI
81   KAAYLQETGK PLDETLKKAL TGHLEEVVLA LLKTPAQFDA
121  DELRAAMKGL GTDEDTLIEI LASRTNKEIR DINRVYREEL
161  KRDLAKDITS DTSGDFRNAL LSLAKGDRSE DFGVNEDLAD
201  SDARALYEAG ERRKGTDVNV FNTILTTRSY PQLRRVFQKY
241  TKYSKHDMNK VLDLELKGDI EKCLTAIVKC ATSKPAFFAE
281  KLHQAMKGVG TRHKALIRIM VSRSEIDMND IKAFYQKMYG
321  ISLCQAILDE TKGDYEKILV ALCGGN
```

Figure 2c

```
1    MNLILRYTFS KMAMVSEFLK QAWFIENEEQ EYVQTVKSSK
41   GGPGSAVSPY PTFNPSSDVA ALHKAIMVKG VDEATIIDIL
81   TKRNNAQRQQ IKAAYLQETG KPLDETLKKA LTGHLEEVVL
121  ALLKTPAQFD ADELRAAMKG LGTDEDTLIE ILASRTNKEI
161  RDINRVYREE LKRDLAKDIT SDTSGDFRNA LLSLAKGDRS
201  EDFG
```

Figure 2d

```
1    MAMVSEFLKQ AWFIENEEQE YVQTVKSSKG GPGSAVSPYP
41   TFNPSSDVAA LHKAIMVKGV DEATIIDILT KRNNAQRQQI
81   KAAYLQETGK PLDETLKKAL TGHLEEVVLA LLKTP
```

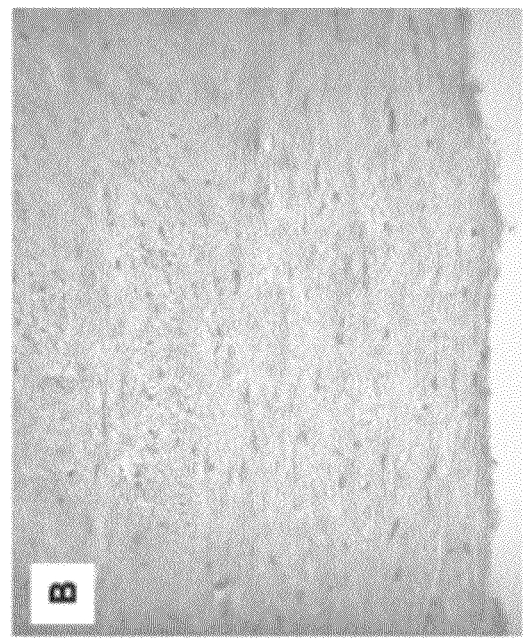
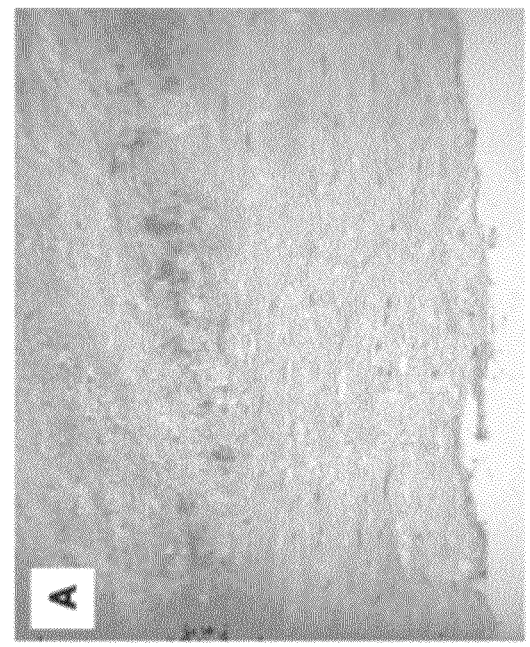
Figure 10

SEQUENCE LISTING

```
<160> NUMBER OF SEQ ID NOS: 27

<210> SEQ ID NO 1
<211> LENGTH: 25
<212> TYPE: PRT
<213> ORGANISM: Homo sapiens
<220> FEATURE:
<221> NAME/KEY: ACETYLATION
<222> LOCATION: (1)..(1)

<400> SEQUENCE: 1

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25

<210> SEQ ID NO 2
<211> LENGTH: 6
<212> TYPE: PRT
<213> ORGANISM: Homo sapiens

<400> SEQUENCE: 2

Ala Met Val Ser Glu Phe
1               5

<210> SEQ ID NO 3
<211> LENGTH: 6
<212> TYPE: PRT
<213> ORGANISM: Homo sapiens

<400> SEQUENCE: 3

Met Val Ser Glu Phe Leu
1               5
```

```
<210> SEQ ID NO 4
<211> LENGTH: 6
<212> TYPE: PRT
<213> ORGANISM: Homo sapiens

<400> SEQUENCE: 4

Val Ser Glu Phe Leu Lys
1               5

<210> SEQ ID NO 5
<211> LENGTH: 6
<212> TYPE: PRT
<213> ORGANISM: Homo sapiens

<400> SEQUENCE: 5

Ser Glu Phe Leu Lys Gln
1               5

<210> SEQ ID NO 6
<211> LENGTH: 6
<212> TYPE: PRT
<213> ORGANISM: Homo sapiens

<400> SEQUENCE: 6

Glu Phe Leu Lys Gln Ala
1               5

<210> SEQ ID NO 7
<211> LENGTH: 6
<212> TYPE: PRT
<213> ORGANISM: Homo sapiens

<400> SEQUENCE: 7

Phe Leu Lys Gln Ala Trp
1               5

<210> SEQ ID NO 8
<211> LENGTH: 6
<212> TYPE: PRT
<213> ORGANISM: Homo sapiens

<400> SEQUENCE: 8

Leu Lys Gln Ala Trp Phe
1               5

<210> SEQ ID NO 9
<211> LENGTH: 6
<212> TYPE: PRT
<213> ORGANISM: Homo sapiens

<400> SEQUENCE: 9

Lys Gln Ala Trp Phe Ile
1               5

<210> SEQ ID NO 10
<211> LENGTH: 6
<212> TYPE: PRT
<213> ORGANISM: Homo sapiens

<400> SEQUENCE: 10

Gln Ala Trp Phe Ile Glu
1               5
```

```
<210> SEQ ID NO 11
<211> LENGTH: 6
<212> TYPE: PRT
<213> ORGANISM: Homo sapiens

<400> SEQUENCE: 11

Ala Trp Phe Ile Glu Asn
1               5

<210> SEQ ID NO 12
<211> LENGTH: 6
<212> TYPE: PRT
<213> ORGANISM: Homo sapiens

<400> SEQUENCE: 12

Trp Phe Ile Glu Asn Glu
1               5

<210> SEQ ID NO 13
<211> LENGTH: 6
<212> TYPE: PRT
<213> ORGANISM: Homo sapiens

<400> SEQUENCE: 13

Phe Ile Glu Asn Glu Glu
1               5

<210> SEQ ID NO 14
<211> LENGTH: 6
<212> TYPE: PRT
<213> ORGANISM: Homo sapiens

<400> SEQUENCE: 14

Ile Glu Asn Glu Glu Gln
1               5

<210> SEQ ID NO 15
<211> LENGTH: 6
<212> TYPE: PRT
<213> ORGANISM: Homo sapiens

<400> SEQUENCE: 15

Glu Asn Glu Glu Gln Glu
1               5

<210> SEQ ID NO 16
<211> LENGTH: 6
<212> TYPE: PRT
<213> ORGANISM: Homo sapiens

<400> SEQUENCE: 16

Asn Glu Glu Gln Glu Tyr
1               5

<210> SEQ ID NO 17
<211> LENGTH: 6
<212> TYPE: PRT
<213> ORGANISM: Homo sapiens

<400> SEQUENCE: 17

Glu Glu Gln Glu Tyr Val
1               5
```

-continued

<210> SEQ ID NO 18
<211> LENGTH: 6
<212> TYPE: PRT
<213> ORGANISM: Homo sapiens

<400> SEQUENCE: 18

Glu Gln Glu Tyr Val Gln
1               5

<210> SEQ ID NO 19
<211> LENGTH: 6
<212> TYPE: PRT
<213> ORGANISM: Homo sapiens

<400> SEQUENCE: 19

Gln Glu Tyr Val Gln Thr
1               5

<210> SEQ ID NO 20
<211> LENGTH: 6
<212> TYPE: PRT
<213> ORGANISM: Homo sapiens

<400> SEQUENCE: 20

Glu Tyr Val Gln Thr Val
1               5

<210> SEQ ID NO 21
<211> LENGTH: 6
<212> TYPE: PRT
<213> ORGANISM: Homo sapiens

<400> SEQUENCE: 21

Tyr Val Gln Thr Val Lys
1               5

<210> SEQ ID NO 22
<211> LENGTH: 21
<212> TYPE: PRT
<213> ORGANISM: Artificial
<220> FEATURE:
<223> OTHER INFORMATION: Myelin Oligodendrocyte Glycoprotein peptide
      (MOG)33-55

<400> SEQUENCE: 22

Met Glu Val Gly Trp Tyr Arg Ser Pro Phe Ser Arg Val Val His Leu
1               5                   10                  15

Tyr Arg Asn Gly Lys
            20

<210> SEQ ID NO 23
<211> LENGTH: 346
<212> TYPE: PRT
<213> ORGANISM: Homo sapiens

<400> SEQUENCE: 23

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

```
Ile Ile Asp Ile Leu Thr Lys Arg Asn Asn Ala Gln Arg Gln Gln Ile
 65                  70                  75                  80

Lys Ala Ala Tyr Leu Gln Glu Thr Gly Lys Pro Leu Asp Glu Thr Leu
                 85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285

Val Gly Thr Arg His Lys Ala Leu Ile Arg Ile Met Val Ser Arg Ser
    290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
                325                 330                 335

Lys Ile Leu Val Ala Leu Cys Gly Gly Asn
            340                 345

<210> SEQ ID NO 24
<211> LENGTH: 1041
<212> TYPE: DNA
<213> ORGANISM: Homo sapiens

<400> SEQUENCE: 24
atggcaatgg tatcagaatt cctcaagcag gcctggttta ttgaaaatga agagcaggaa        60
tatgttcaaa ctgtgaagtc atccaaaggt ggtcccggat cagcggtgag ccccatcct       120 accttcaatc atcctcgga tgtcgctgcc ttgcataagg ccataatggt taaaggtgtg       180
gatgaagcaa ccatcattga cattctaact aagcgaaaca atgcacagcg tcaacagatc       240
aaagcagcat atctccagga acaggaaag cccctggatg aaacactgaa gaaagccctt       300
acaggtcacc ttgaggaggt tgttttggct ctgctaaaaa ctccagcgca atttgatgct       360
gatgaacttc gtgctgccat gaagggcctt ggaactgatg aagatactct aattgagatt       420
ttggcatcaa gaactaacaa agaaatcaga gacattaaca gggtctacag agaggaactg       480
aagagagatc tggccaaaga cataaccctca gacacatctg gagattttcg gaacgctttg       540
```

-continued

```
cttttctcttg ctaagggtga ccgatctgag gactttggtg tgaatgaaga cttggctgat      600
tcagatgcca gggccttgta tgaagcagga gaaaggagaa aggggacaga cgtaaacgtg      660
ttcaatacca tccttaccac cagaagctat ccacaacttc gcagagtgtt tcagaaatac      720
accaagtaca gtaagcatga catgaacaaa gttctggacc tggagttgaa aggtgacatt      780
gagaaatgcc tcacagctat cgtgaagtgc gccacaagca aaccagcttt ctttgcagag      840
aagcttcatc aagccatgaa aggtgttgga actcgccata aggcattgat caggattatg      900
gtttcccgtt ctgaaattga catgaatgat atcaaagcat tctatcagaa gatgtatggt      960
atctcccttt gccaagccat cctggatgaa accaaggag attatgagaa atcctggtg       1020 gctctttgtg gaggaaacta a                                                1041
```

<210> SEQ ID NO 25
<211> LENGTH: 346
<212> TYPE: PRT
<213> ORGANISM: Homo sapiens

<400> SEQUENCE: 25

```
Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
    50                  55                  60

Ile Ile Asp Ile Leu Thr Lys Arg Asn Asn Ala Gln Arg Gln Gln Ile
65                  70                  75                  80

Lys Ala Ala Tyr Leu Gln Glu Thr Gly Lys Pro Leu Asp Glu Thr Leu
                85                  90                  95

Lys Lys Ala Leu Thr Gly His Leu Glu Glu Val Val Leu Ala Leu Leu
            100                 105                 110

Lys Thr Pro Ala Gln Phe Asp Ala Asp Glu Leu Arg Ala Ala Met Lys
        115                 120                 125

Gly Leu Gly Thr Asp Glu Asp Thr Leu Ile Glu Ile Leu Ala Ser Arg
    130                 135                 140

Thr Asn Lys Glu Ile Arg Asp Ile Asn Arg Val Tyr Arg Glu Glu Leu
145                 150                 155                 160

Lys Arg Asp Leu Ala Lys Asp Ile Thr Ser Asp Thr Ser Gly Asp Phe
                165                 170                 175

Arg Asn Ala Leu Leu Ser Leu Ala Lys Gly Asp Arg Ser Glu Asp Phe
            180                 185                 190

Gly Val Asn Glu Asp Leu Ala Asp Ser Asp Ala Arg Ala Leu Tyr Glu
        195                 200                 205

Ala Gly Glu Arg Arg Lys Gly Thr Asp Val Asn Val Phe Asn Thr Ile
    210                 215                 220

Leu Thr Thr Arg Ser Tyr Pro Gln Leu Arg Arg Val Phe Gln Lys Tyr
225                 230                 235                 240

Thr Lys Tyr Ser Lys His Asp Met Asn Lys Val Leu Asp Leu Glu Leu
                245                 250                 255

Lys Gly Asp Ile Glu Lys Cys Leu Thr Ala Ile Val Lys Cys Ala Thr
            260                 265                 270

Ser Lys Pro Ala Phe Phe Ala Glu Lys Leu His Gln Ala Met Lys Gly
        275                 280                 285
```

```
Val Gly Thr Arg His Lys Ala Leu Ile Arg Ile Met Val Ser Arg Ser
290                 295                 300

Glu Ile Asp Met Asn Asp Ile Lys Ala Phe Tyr Gln Lys Met Tyr Gly
305                 310                 315                 320

Ile Ser Leu Cys Gln Ala Ile Leu Asp Glu Thr Lys Gly Asp Tyr Glu
            325                 330                 335

Lys Ile Leu Val Ala Leu Cys Gly Gly Asn
            340                 345

<210> SEQ ID NO 26
<211> LENGTH: 204
<212> TYPE: PRT
<213> ORGANISM: Homo sapiens

<400> SEQUENCE: 26

Met Asn Leu Ile Leu Arg Tyr Thr Phe Ser Lys Met Ala Met Val Ser
1               5                   10                  15

Glu Phe Leu Lys Gln Ala Trp Phe Ile Glu Asn Glu Glu Gln Glu Tyr
            20                  25                  30

Val Gln Thr Val Lys Ser Ser Lys Gly Gly Pro Gly Ser Ala Val Ser
        35                  40                  45

Pro Tyr Pro Thr Phe Asn Pro Ser Ser Asp Val Ala Ala Leu His Lys
50                  55                  60

Ala Ile Met Val Lys Gly Val Asp Glu Ala Thr Ile Ile Asp Ile Leu
65                  70                  75                  80

Thr Lys Arg Asn Asn Ala Gln Arg Gln Gln Ile Lys Ala Ala Tyr Leu
                85                  90                  95

Gln Glu Thr Gly Lys Pro Leu Asp Glu Thr Leu Lys Lys Ala Leu Thr
            100                 105                 110

Gly His Leu Glu Glu Val Val Leu Ala Leu Leu Lys Thr Pro Ala Gln
        115                 120                 125

Phe Asp Ala Asp Glu Leu Arg Ala Ala Met Lys Gly Leu Gly Thr Asp
    130                 135                 140

Glu Asp Thr Leu Ile Glu Ile Leu Ala Ser Arg Thr Asn Lys Glu Ile
145                 150                 155                 160

Arg Asp Ile Asn Arg Val Tyr Arg Glu Glu Leu Lys Arg Asp Leu Ala
                165                 170                 175

Lys Asp Ile Thr Ser Asp Thr Ser Gly Asp Phe Arg Asn Ala Leu Leu
            180                 185                 190

Ser Leu Ala Lys Gly Asp Arg Ser Glu Asp Phe Gly
        195                 200

<210> SEQ ID NO 27
<211> LENGTH: 115
<212> TYPE: PRT
<213> ORGANISM: Homo sapiens

<400> SEQUENCE: 27

Met Ala Met Val Ser Glu Phe Leu Lys Gln Ala Trp Phe Ile Glu Asn
1               5                   10                  15

Glu Glu Gln Glu Tyr Val Gln Thr Val Lys Ser Ser Lys Gly Gly Pro
            20                  25                  30

Gly Ser Ala Val Ser Pro Tyr Pro Thr Phe Asn Pro Ser Ser Asp Val
        35                  40                  45

Ala Ala Leu His Lys Ala Ile Met Val Lys Gly Val Asp Glu Ala Thr
50                  55                  60
```

-continued

```
Ile Ile Asp Ile Leu Thr Lys Arg Asn Asn Ala Gln Arg Gln Gln Ile
65              70                  75                  80

Lys Ala Ala Tyr Leu Gln Glu Thr Gly Lys Pro Leu Asp Glu Thr Leu
            85                  90                  95

Lys Lys Ala Leu Thr Gly His Leu Glu Glu Val Val Leu Ala Leu Leu
            100                 105                 110

Lys Thr Pro
        115
```

TREATMENT OF AUTOIMMUNE DISEASE BY MODULATING ANNEXIN-1 (LIPOCORTIN 1)

CROSS-REFERENCE TO RELATED APPLICATIONS

This application is the U.S. National Stage filing of International Application Serial No. PCT/GB2009/002810 filed Dec. 2, 2009, which claims priority to GB 0822011.3 filed Dec. 2, 2008, each of which is incorporated herein by reference in its entirety.

The present invention relates to methods for treating T cell-mediated disease by modulating the activity of Annexin-1.

Autoimmune diseases are chronic disabling pathologies caused by malfunction of the immune system. In most cases they are initiated by an uncontrolled T cell response to autoantigens presented in the context of MHC molecules of antigen presenting cells (APCs). Several factors have been described as being involved in the pathogenesis of autoimmune diseases including environmental, genetic and viral factors, with one overarching feature: the hyperresponsivity of T cells.

Glucocorticoids (GCs) are often used for the therapy of a variety of chronic autoimmune diseases because of their ability to simultaneously block both the innate and adaptive immune response. Studies over the last 10 years or so by the present inventors and other research groups have shown that some of the inflammatory effects of GCs on the innate immune response are mediated by a protein called Annexin-1 (Anx-A1). This protein has been proven to exert a homeostatic control over a number of cell types including neutrophils, macrophages and endothelial cells. However, one aspect that has always been neglected is the role of Anx-A1 in the adaptive immune response. This is surprising considering that Anx-A1 has been proposed as one of the second messengers of the pharmacological effects of GCs.

The present inventors have previously shown that Anx-A1 plays a homeostatic role in T cells by modulating the strength of T cell receptor (TCR) signaling (D'Acquisto et al., Blood 109: 1095-1102, 2007).

Furthermore, the inventors have shown that high levels of Anx-A1 lower the threshold of T cell activation and favour the differentiation into Th1 cells, whereas Anx-A1 deficient mice show impaired T cell activation and increased differentiation into Th2 cells (D'Acquisto et al., Eur. J. Immunol. 37: 3131-3142, 2007).

WO 2005/027965 describes the discovery of a mechanism by which apoptotic neutrophils deliver anti-inflammatory signals to dendritic cells and identifies an antibody that interferes with this process. In particular, WO 2005/027965 describes the identification of Anx-1 as a signalling molecule which is said to be expressed by apoptotic neutrophils to inhibit the activation and maturation of dendritic cells. WO 2005/027965 proposes that an antibody termed DAC5 (Detector of Apoptotic Cells Nr. 5) recognizes and blocks the anti-inflammatory effects of Anx-1 presented on the surface of apoptotic neutrophils upon phagocytosis by dendritic cells. WO 2005/027965 thus refers to the possibility of treatment of various diseases by targeting such apoptotic cells and deleting them by causing an inflammatory response, but does not discuss a role for Anx-1 in T cell activation.

WO 2005/027965 claims that annexins are expressed on cells that are undergoing apoptosis (see for example page 8, lines 6-7 and 29-30) and that these annexins are presented on the surface of such cells (see for example page 6, lines 10-11 and page 8, lines 16-17). However, two separate studies (Maderna et al., J Immunol., 174: 3727-3733, 2005; Scannell et al., J Immunol., 178: 4595-4605, 2007) have shown that apoptotic cells, including neutrophils, release annexin-1, rather than expressing the protein and presenting it on the cell surface. Since annexin-1 is released from the cell, it cannot be claimed that DAC5 would identify only apoptotic cells expressing the protein on the surface, as the antibody would also identify released annexin-1.

Furthermore, WO 2005/027965 claims that co-incubation of apoptotic neutrophils expressing annexin-1 on their cell membrane with dendritic cells activated with LPS causes inhibition of TNF-α secretion and upregulation of the activation markers CD83, CD86 and HLA-DR, and that addition of DAC5 to this culture reverses the inhibitory effects of the annexin-1 expressing apoptotic neutrophils (page 5, line 31 to page 6, line 8). Data from the present inventors (Huggins et al., FASEB J. 2008, in press) demonstrates that dendritic cells release Anx-1 upon stimulation with LPS and thus the DAC5 described in WO 2005/027965 would bind the Anx-1 externalized on the neutrophils as well as the annexin-1 released by dendritic cells. Furthermore, the present inventors have found that the absence of annexin-1 in dendritic cells causes an increased expression of maturation/activation markers and production of inflammatory cytokines such as TNF-α and IL-1β and IL-12. Therefore, the antibody DAC5 described in WO 2005/027965 should affect the maturation and activation of dendritic cells and thus the subsequent modulation of the immune response.

In support of this, the present inventors have shown that co-culturing Anx-A1$^{-/-}$ dendritic cells with naïve T cells within a mixed lymphocyte reaction (MLR) showed a significantly reduced ability to induce either T cell proliferation or IL-2 and IFN-γ production. Thus, agents blocking Anx-A1 function in dendritic cells should reduce their capacity to stimulate a robust T cell mediated immune response. The antibodies referred to in WO 2005/027965 would therefore not be suitable for treating the diseases referred to in that patent application.

The present invention provides the use of specific binding molecules which bind to Annexin-1 (Anx-A1) in the treatment of T cell-mediated disease.

According to a first aspect of the invention there is therefore provided a specific binding molecule which binds to Annexin-1 (Anx-A1) for use in the treatment of T cell-mediated disease.

The present inventors have previously shown that Anx-A1 modulates the strength of T cell receptor (TCR) signaling and that high levels of Anx-A1 lower the threshold of T cell activation and favour differentiation into Th1 cells. The inventors have now identified the annexin pathway, and the ensuing signal, as a target for blockade in order to treat T cell-mediated diseases. Such diseases include those in which there is aberrant T cell activation, for example many autoimmune diseases, and those in which it is desirable to skew differentiation of T cells in favour of Th1 rather than Th2 cells.

The present invention utilises a specific binding molecule which binds to Annexin-1 (Anx-A1).

Annexins are a group of calcium- and phospholipid-binding cellular proteins and are also known as lipocortins. The annexin family has 13 members, including Annexin A1, Annexin A2 and Annexin A5. Annexin-A1 is also known as Annexin-1 and is referred to herein as "Anx-A1". Annexin-1 (Anx-A1) is a 37-kDa protein and was originally described as a mediator of the actions of glucocorticoids. Over the last few years evidence has shown than Anx-A1 plays a homeostatic role in the adaptive immune system, in particular T cells, by modulating the strength of T cell receptor (TCR) signalling. Anx-A1 acts as an endogenous down-regulator of inflammation in cells of the innate immune system in vivo. FIG. 1A is a ribbon diagram showing the three-dimensional structure of Anx-A1.

There are eight human nucleotide sequences which encode Anx-A1. Of these, only four are translated and thus there are four isoforms of Anx-A1, designated ANXA1-002, ANXA1-003, ANXA1-004 and ANXA1-006. These sequences are available from the Ensembl website (www.ensembl.org) and are designated OTTHUMT00000052664 (ANXA1-002), OTTHUMT00000052665 (ANXA1-003), OTTHUMT00000052666 (ANXA1-004) and OTTHUMT00000052668 (ANXA1-006). The amino acid and nucleotide sequences of one isoform of human Annexin-1 (Anx-A1), ANXA1-003, are shown in FIG. 2a. The amino acid sequences of isoforms ANXA1-002, ANXA1-004 and ANXA1-006 are shown in FIGS. 2b, 2c and 2d respectively. As can be seen from FIG. 2, isoforms ANXA1-002, ANXA1-004 and ANXA1-006 are either short splice variants of ANXA1-003 or variants of ANXA1-003 with a small number of amino acid changes.

A number of studies have shown that an N-terminal peptide of Anx-A1 named Ac.2-26 acts as a bioactive surrogate of the whole protein (see e.g. Lim et al., Proc Natl Acad Sci USA 95, 14535-9, 1998).

FIG. 1B is a schematic representation of the annexin repeats and the location of this bioactive sequence. Peptide Ac.2-26 is an acetylated peptide having the sequence of amino acid residues 2-26 of the full-length amino acid sequence of Anx-A1 shown in FIG. 2. The sequence of peptide Ac.2-26 is shown in FIG. 1 C (SEQ ID NO:1) and is as follows:

CH₃CO-AMVSEFLKQA WFIENEEQEYVQTVK (SEQ ID NO: 1)

Anx-A1 and its N-terminal derived bioactive peptides mediate their biological effects through members of the formyl peptide receptor (FPR) family. Anx-A1 exerts its counterregulatory actions on neutrophil extravasation and innate immunity by direct binding and activation of one member of this family, formyl peptide receptor like-1 (FPRL-1). The present inventors have previously found that stimulation of T cells in the presence of hrAnx-A1 increases T cell activation via stimulation of FPRL-1 (D'Acquisto et at, Blood 109: 1095-1102, 2007).

The present invention utilises a specific binding molecule which binds to Annexin-1 (Anx-A1). The Anx-A1 to which the specific binding molecule binds is typically human Anx-A1 having the polypeptide sequence shown in FIG. 2a i) (SEQ ID NO:23) and ii) (SEQ ID NO:24), or a variant or fragment thereof, such as one of the isoforms of human Anx-A1 having the polypeptide sequence shown in FIG. 2b (SEQ ID NO:25), FIG. 2c (SEQ ID NO:26) or FIG. 2d (SEQ ID NO:27). The fragment of human Anx-A1 to which the specific binding molecule binds is typically the polypeptide having the sequence shown in FIG. 1C. The Anx-A1 to which the specific binding molecule binds is typically encoded by the nucleotide sequence shown in FIG. 2a.

As used herein the term "variant" relates to proteins which have a similar amino acid sequence and/or which retain the same function. For instance, the term "variant" encompasses proteins or polypeptides which include one or more amino acid additions, deletions, substitutions or the like. Amino acid substitutions are typically conservative substitutions, i.e. the substitution of an amino acid with another with generally similar properties, such that the overall functioning is likely not to be seriously affected.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Using the three letter and one letter codes the amino acids may be referred to as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and references to glutamic acid include glutamate, unless the context specifies otherwise.

Amino acid deletions or insertions may also be made relative to the amino acid sequence of the protein referred to above. Thus, for example, amino acids which do not have a substantial effect on the activity of the polypeptide, or at least which do not eliminate such activity, may be deleted. Such deletions can be advantageous since the overall length and the molecular weight of a polypeptide can be reduced whilst still retaining activity. This can enable the amount of polypeptide required for a particular purpose to be reduced—for example, dosage levels can be reduced.

Amino acid insertions relative to the sequence of the fusion protein above can also be made. This may be done to alter the properties of a substance (e.g. to assist in identification, purification or expression).

Amino acid changes relative to the sequence given above can be made using any suitable technique e.g. by using site-directed mutagenesis or solid state synthesis.

It should be appreciated that amino acid substitutions or insertions within the scope of the present invention can be made using naturally occurring or non-naturally occurring amino acids. Whether or not natural or synthetic amino acids are used, it is preferred that only L-amino acids are present.

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

Variants of the proteins and polypeptides described herein should retain the function of the original protein or polypeptide. Alternatively or in addition to retaining the function of the original protein or polypeptide, variants of the proteins and polypeptides described herein typically have at least 60% identity (as discussed above) with the proteins or polypeptides described herein, in particular the polypeptide sequences shown in FIG. 1C or FIG. 2. Typically, variants for use in the invention have at least 70%, at least 80%, at least 90%, at least 95%, at least 97% or at least 99% identity to the proteins or polypeptides described herein, in particular the polypeptide sequences shown in FIG. 1C or FIG. 2.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

In an alternative approach, the variants can be fusion proteins, incorporating moieties which render purification easier, for example by effectively tagging the desired protein or polypeptide. It may be necessary to remove the "tag" or it may be the case that the fusion protein itself retains sufficient functionality to be useful.

A "specific binding molecule which binds to Anx-A1" as used herein is a molecule which binds with greater affinity to Anx-A1 than to other molecules, i.e. which binds specifically to Anx-A1. Specific binding molecules which bind to Anx-A1 include anti-Anx-A1 antibodies and aptamers. The anti-Anx-A1 antibodies for use in the present invention function by blocking the activation of T cells and thus, when administered, can be used in the treatment of T cell-mediated diseases, which are typically caused by aberrant T cell activation.

Anti-Anx-A1 antibodies can be raised, for example, against human Anx-A1 having the amino acid sequence set out in FIG. 2, typically the amino acid sequence set out in FIG. 2a. Alternatively, anti-Anx-A1 antibodies can be directed to a particular epitope or epitopes of human Anx-A1 having the amino acid sequence set out in FIG. 2, typically the amino acid sequence set out in FIG. 2a. For example, anti-Anx-A1 antibodies can be directed against an N-terminal fragment of Anx-A1, for example an N-terminal fragment of at least 188, 100, 50 or 25 amino acid residues from the N-terminus of the amino acid sequence set out in FIG. 2a. Typically, the anti-Anx-A1 antibody for use in the invention is an antibody against the N-terminal fragment of Anx-A1 termed Ac2-26 and which has the sequence shown in FIG. 1C, or against a fragment of at least 6 amino acids thereof. Specific binding molecules which bind to Anx-A1 therefore include anti-Anx-A1 antibodies which are antibodies against the Anx-A1 fragment Ac2-26 having the sequence shown in FIG. 1C or a fragment of at least 6 amino acids thereof. In this embodiment, the anti-Anx-A1 antibody is raised against a fragment of the sequence shown in FIG. 1C which is antigenic and capable of stimulating the production of antibodies which, when administered, can be used in the treatment of T cell-mediated diseases, which are typically caused by aberrant T cell activation.

As stated above, an active subfragment of the specified sequence may be used as defined. Active subfragments may consist of or include a fragment of at least 6 continuous amino acid residues (a hexapeptide) of the N-terminal fragment of Anx-A1 termed Ac2-26 having the sequence set out in FIG. 1C, including one or more of:

```
AMVSEF (SEQ ID NO: 2)
MVSEFL (SEQ ID NO: 3)
VSEFLK (SEQ ID NO: 4)
SEFLKQ (SEQ ID NO: 5)
EFLKQA (SEQ ID NO: 6)
FLKQAW (SEQ ID NO: 7)
LKQAWF (SEQ ID NO: 8)
KQAWFI (SEQ ID NO: 9)
QAWFIE (SEQ ID NO: 10)
AWFIEN (SEQ ID NO: 11)
WFIENE (SEQ ID NO: 12)
FIENEE (SEQ ID NO: 13)
IENEEQ (SEQ ID NO: 14)
ENEEQE (SEQ ID NO: 15)
NEEQEY (SEQ ID NO: 16)
EEQEYV (SEQ ID NO: 17)
EQEYVQ (SEQ ID NO: 18)
QEYVQT (SEQ ID NO: 19)
EYVQTV (SEQ ID NO: 20)
YVQTVK (SEQ ID NO: 21)
```

Active subfragments may consist of or include a fragment of more than 6 continuous amino acid residues of the N-terminal fragment of Anx-A1 termed Ac2-26 having the sequence set out in FIG. 1C, for example a fragment of at least 7, at least 8, at least 9, at least 10, at least 11, at least 12, at least 13, at least 14, at least 15, at least 16, at least 17, at least 18, at least 19, at least 20, at least 21, at least 22, at least 23 or at least 24 amino acids of the sequence set out in FIG. 1C.

Anti-Anx-A1 antibodies include monoclonal and polyclonal antibodies. Typically, the anti-Anx-A1 antibody is a monoclonal antibody. The anti-Anx-A1 antibody can be a commercially available antibody, for example a rabbit polyclonal or mouse monoclonal antibody. Typically, the anti-Anx-A1 antibody is humanised, as described in detail below.

Monoclonal antibodies can be produced from hybridomas. These are typically formed by fusing myeloma cells and spleen cells which produce the desired antibody in order to form an immortal cell line. The well-known Kohler & Milstein technique (*Nature* 256:495-497 (1975)) or subsequent variations upon this technique can be used to produce a monoclonal antibody for use in accordance with the invention.

Polyclonal antibodies can be raised by stimulating their production in a suitable animal host (e.g. a mouse, rat, guinea pig, rabbit, sheep, goat or monkey) by injection of Anx-A1, or a variant or fragment thereof, into the animal. If desired, an adjuvant may be administered together with the Anx-A1 protein. Well-known adjuvants include Freund's adjuvant (complete and incomplete) and aluminium hydroxide. The antibodies can then be purified by virtue of their binding to Anx-A1.

Techniques for producing monoclonal and polyclonal antibodies that bind to a particular polypeptide/protein are now well developed in the art and are discussed in standard immunology textbooks, for example in Roitt et al, *Immunology* second edition (1989), Churchill Livingstone, London.

In addition to whole antibodies, the present invention includes derivatives thereof which are capable of binding to Anx-A1 as described herein. Thus the present invention includes antibody fragments and synthetic constructs. Examples of antibody fragments and synthetic constructs are given by Dougall et at in *Trends Biotechnol.*, 12: 372-379 (1994).

Antibody fragments include, for example, Fab, F(ab')$_2$ and Fv fragments. Fab fragments are discussed in Roitt et at [supra]. Fv fragments can be modified to produce a synthetic construct known as a single chain Fv (scFv) molecule. This includes a peptide linker covalently joining variable heavy chain ($V_H$) and variable light chain ($V_L$) regions, which contributes to the stability of the molecule. The linker may comprise from 1 to 20 amino acids, such as for example 1, 2, 3 or 4 amino acids, 5, 10 or 15 amino acids, or other intermediate numbers in the range 1 to 20 as convenient. The peptide linker may be formed from any generally convenient amino acid residues, such as glycine and/or serine. One example of a suitable linker is Gly$_4$Ser. Multimers of such linkers may be used, such as for example a dimer, a trimer, a tetramer or a pentamer, e.g. (Gly$_4$Ser)$_2$, (Gly$_4$Ser)$_3$, (Gly$_4$Ser)$_4$ or (Gly$_4$Ser)$_5$. However, in other embodiments no peptide linker is present and the $V_L$ domain is linked to the $V_H$ domain by a peptide bond.

The specific binding molecule may be an analogue of a single-chain variable fragment (scFv). For example, the scFv may be linked to other specific binding molecules (for example other scFvs, Fab antibody fragments and chimeric IgG antibodies (e.g. with human frameworks)). The scFv may be linked to other scFvs so as to form a multimer which is a multi-specific binding protein, for example a dimer, a trimer or a tetramer. Bi-specific scFv's are sometimes referred to as diabodies, tri-specific as triabodies and tetra-specific as tetrabodies.

An scFv can be prepared by any suitable technique using standard chemical or molecular biology techniques. In one embodiment of the invention, the monoclonal antibody analogues can be prepared as scFv's from a naïve human antibody phage display library (McCafferty et al., *Nature* 348, 552-554 (1990); and as described in WO 92/01047).

Other synthetic constructs that can be used include Complementarity Determining Region (CDR) peptides. These are synthetic peptides comprising antigen-binding determinants. Peptide mimetics can also be used. These molecules are usually conformationally restricted organic rings that mimic the structure of a CDR loop and that include antigen-interactive side chains.

Synthetic constructs include chimeric molecules. Thus, humanised antibodies or derivatives thereof are within the scope of the antibodies for use in the present invention. Methods for humanising antibodies are well known in the art. The antibody can be humanised by modifying the amino acid sequence of the antibody. An example of a humanised antibody is an antibody having human framework regions, but rodent (for example murine) hypervariable regions. Ways of producing chimeric antibodies are discussed for example by Morrison et al in PNAS, 81: 6851-6855 (1984) and by Takeda et al in Nature, 314: 452-454 (1985). Humanisation can be performed, for example, as described by Jones et al in Nature, 321: 522-525 (1986); Verhoeyen et al in Science, 239: 1534-1536; Riechmann et al in Nature 332: 323-327, 1988. Methods to reduce the immunogenicity of the specific binding molecules of the invention may include CDR grafting on to a suitable antibody framework scaffold or variable surface residue remodelling, e.g. by site-directed mutagenesis or other commonly used molecular biological techniques (Roguska et al *Protein Eng.* 9 895-904 (1996)).

Other methods applicable include the identification of potential T-cell epitopes within the molecule, and the subsequent removal of these e.g. by site-directed mutagenesis (de-immunisation). Humanisation of the CDR regions or of the surrounding framework sequence may be carried out as desired.

Synthetic constructs also include molecules comprising an additional moiety that provides the molecule with some desirable property in addition to antigen binding. For example the moiety may be a label (e.g. a fluorescent or radioactive label). Alternatively, it may be a pharmaceutically active agent.

The present invention relates to the use of a specific binding molecule which binds to Anx-A1 for the treatment of T cell-mediated disease.

The present invention can be used to treat a wide range of diseases which are mediated by T cells. In the present context, "T cell-mediated disease" means any disease or condition in which T cells play a role in pathogenesis or development of the disease or condition. T cell-mediated diseases are typically caused by aberrant T cell activation. Accordingly, such diseases can be treated by preventing the activation of T cells by blocking the activity of Anx-A1. Typically, the T cell-mediated diseases treated in the present invention are diseases in which Th1 cells play a role.

T cell-mediated diseases include but are not limited to graft-versus-host disease, graft rejection, atherosclerosis, HIV and/or AIDS, psoriasis and some autoimmune diseases. Autoimmune diseases which can be treated according to the present invention include rheumatoid arthritis (RA), multiple sclerosis (MS), systemic lupus erythematosus (SLE), Addison's disease, Grave's disease, scleroderma, polymyositis, some forms of diabetes mellitus (for example juvenile onset diabetes), autoimmune uveoretinitis, ulcerative colitis, pemphigus vulgaris, inflammatory bowel disease and autoimmune thyroiditis. The T cell-mediated disease is typically rheumatoid arthritis, multiple sclerosis, systemic lupus erythematosus or atherosclerosis.

The T cell-mediated disease is typically rheumatoid arthritis. In rheumatoid arthritis (RA), it is thought that T cells recognise and interact with antigen presenting cells in the synovium. Once activated, these cells produce cytokines and effector molecules; this sequential, expanded production of cytokines constitutes the "cytokine cascade" that results in the activation of macrophages and induction of the inflammatory process, culminating in degradation and resorption of cartilage and bone. Over time, bone erosion, destruction of cartilage, and complete loss of joint integrity can occur. Eventually, multiple organ systems may be affected.

In another embodiment, the T cell-mediated disease is atherosclerosis. Inflammation plays a key role in coronary artery disease and other manifestations of atherosclerosis. Immune cells dominate early atherosclerotic lesions, their effector molecules accelerate progression of the lesions, and activation of inflammation can elicit acute coronary syndromes. Adaptive immunity is highly involved in atherogenesis since it has been shown to interact with metabolic risk factors to initiate, propagate, and activate lesions in the arterial tree.

Two mouse models with features of hypercholesterolemia and rapid development of atherosclerosis, the ApoE$^{-/-}$ and the low-density lipoprotein receptor-knockout mouse (LDLR$^{-/-}$), are useful in the study of atherosclerosis as they mimic the cellular composition of human lesions, particularly in content of T lymphocytes. Lymphocyte recruitment is increased in the arteries of the atherosclerotic-prone ApoE$^{-/-}$ mice even well before the onset of the pathology.

The presence of T-lymphocytes has functional consequences as their complete absence reduces lesion formation during moderate hypercholesterolemia. CD4+ IFN-γ-secreting type-1 helper (Th1) cells are the predominant type of T cell found in plaques, and these T cells exert pro-atherogenic and plaque-destabilising effects.

The inventors have now found that Anx-A1 is expressed in both human and murine atherosclerotic plaques and that there is a correlation between Anx-A1 expression and MS in a mouse model.

In another embodiment, the T cell-mediated disease is systemic lupus erythematosus (SLE). The inventors have now found that Anx-A1 mRNA and protein are expressed at higher levels in T cells from SLE patients than in T cells from healthy volunteers.

In relation to the ability of Anx-A1 to favour differentiation of Th1 cells, the present invention can also be used, for example, to limit uncontrolled protective cellular (Th1) responses against intracellular pathogens and to treat extracellular infection (Th2 response) by suppressing Th1 differentiation and favouring Th2 differentiation.

The specific binding molecule which binds to Anx-A1 is typically formulated for use with a pharmaceutically acceptable carrier, excipient, vehicle, adjuvant and/or diluent. The present invention thus encompasses a pharmaceutical composition comprising a specific binding molecule which binds to Annexin-1 (Anx-A1) for use in the treatment of T cell-mediated disease. The pharmaceutical composition comprises a specific binding molecule which binds to Annexin-1 (Anx-A1) and a pharmaceutically acceptable carrier, excipient, vehicle, adjuvant and/or diluent. Such compositions may be prepared by any method known in the art of pharmacy, for example by admixing the active ingredient with the carrier, excipient, vehicle, adjuvant and/or diluent under sterile conditions.

Suitable carriers, vehicles, adjuvants and/or diluents are well known in the art and include saline, phosphate buffered saline (PBS), carboxymethylcellulose (CMC), methylcellulose, hydroxypropylmethylcellulose (HPMC), dextrose, liposomes, polyvinyl alcohol, pharmaceutical grade starch, mannitol, lactose, magnesium stearate, sodium saccharin, talcum, cellulose, glucose, sucrose (and other sugars), magnesium carbonate, gelatin, oil, alcohol, detergents, emulsifiers or water (preferably sterile). The specific binding molecule which binds to Anx-A1 can be formulated as a liquid formulation, which will generally consist of a suspension or solution of the specific binding molecule which binds to Anx-A1 in a suitable aqueous or non-aqueous liquid carrier or carriers, for example water, ethanol, glycerine, polyethylene glycol (PEG) or an oil.

Typically, when the specific binding molecule which binds to Anx-A1 is an antibody, the antibody is PEGylated, i.e. covalently attached to a polyethylene glycol. Typically, this has the effect of reducing the immunogenicity and increasing the half-life of said antibody.

The specific binding molecule which binds to Anx-A1 can be administered alone or together with another agent.

The specific binding molecule which binds to Anx-A1 for use in the present invention is typically administered to a subject in a therapeutically effective amount. Such an amount is an amount effective to ameliorate, eliminate or prevent one or more symptoms of T cell-mediated disease. Preferably, the subject to be treated is a human. However, the present invention is equally applicable to human or veterinary medicine. For example, the present invention may find use in treating companion animals, such as dogs and cats, or working animals, such as race horses.

The specific binding molecule which binds to Anx-A1 can be administered to the subject by any suitable means. The specific binding molecule which binds to Anx-A1 can be administered systemically, in particular intra-articularly, intra-arterially, intraperitoneally (i.p.), intravenously or intramuscularly. However, the specific binding molecule which binds to Anx-A1 can also be administered by other enteral or parenteral routes such as by subcutaneous, intradermal, topical (including buccal, sublingual or transdermal), oral (including buccal or sublingual), nasal, vaginal, anal, pulmonary or other appropriate administration routes.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions, oils (e.g. vegetable oils) may be used to provide oil-in-water or water in oil suspensions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in *Pharmaceutical Research,* 3(6):318 (1986).

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes.

Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts, buffers, coating agents or antioxidants. They may also contain therapeutically active agents in addition to the specific binding molecule which binds to Anx-A1.

The dose of the specific binding molecule which binds to Anx-A1 to be administered may be determined according to various parameters, especially according to the specific binding molecule which binds to Anx-A1 used; the age, weight and condition of the patient to be treated; the route of administration; and the required regimen. A physician will be able to determine the required route of administration and dosage for a particular patient.

This dosage may be repeated as often as appropriate. If side effects develop the amount and/or frequency of the dosage can be reduced, in accordance with normal clinical practice.

For administration to mammals, and particularly humans, it is expected that the daily dosage of the active agent will be from 1 μg/kg to 10 mg/kg body weight, typically around 10 μg/kg to 1 mg/kg body weight. The physician in any event will determine the actual dosage which will be most suitable for an individual which will be dependant on factors including the age, weight, sex and response of the individual. The above dosages are exemplary of the average case. There can, of course, be instances where higher or lower dosages are merited, and such are within the scope of this invention In a second aspect of the invention, there is provided the use of a specific binding molecule which binds to Anx-A1 in the manufacture of a medicament for the treatment of T cell-mediated disease.

In a third aspect of the invention, there is provided a method for the treatment of T cell-mediated disease comprising administering to a subject in need thereof a therapeutic amount of a specific binding molecule which binds to Anx-A1. As stated above, the method of treatment may of a human or an animal subject and the invention extends equally to methods of treatment for use in human and/or veterinary medicine.

Preferred features for the second and third aspects of the invention are as for the first aspect *mutatis mutandis*.

The invention will now be further described by way of reference to the following Examples and Figures which are provided for the purposes of illustration only and are not to be construed as limiting on the invention. Reference is made to a number of Figures, in which:

FIG. 1A is a ribbon diagram of annexin-1 structure showing the four annexin repeats and the N-terminal domain. FIG. 1B is a schematic representation of the annexin repeats and the location of the bioactive sequence, Annexin-1 peptide Ac.2-26. FIG. 1C shows the amino acid sequence of peptide Ac.2-26, which is an acetylated N-terminal peptide fragment of Anx-A1.

FIG. 2a shows (i) the amino acid sequence and (ii) the nucleotide sequence of human Annexin-1 (Anx-A1), isoform ANXA1-003. FIG. 2b shows the amino acid sequence of human Annexin-1 (Anx-A1), isoform ANXA1-002. FIG. 2c shows the amino acid sequence of human Annexin-1 (Anx-A1), isoform ANXA1-004. FIG. 2d shows the amino acid sequence of human Annexin-1 (Anx-A1), isoform ANXA1-006.

Figure 6:
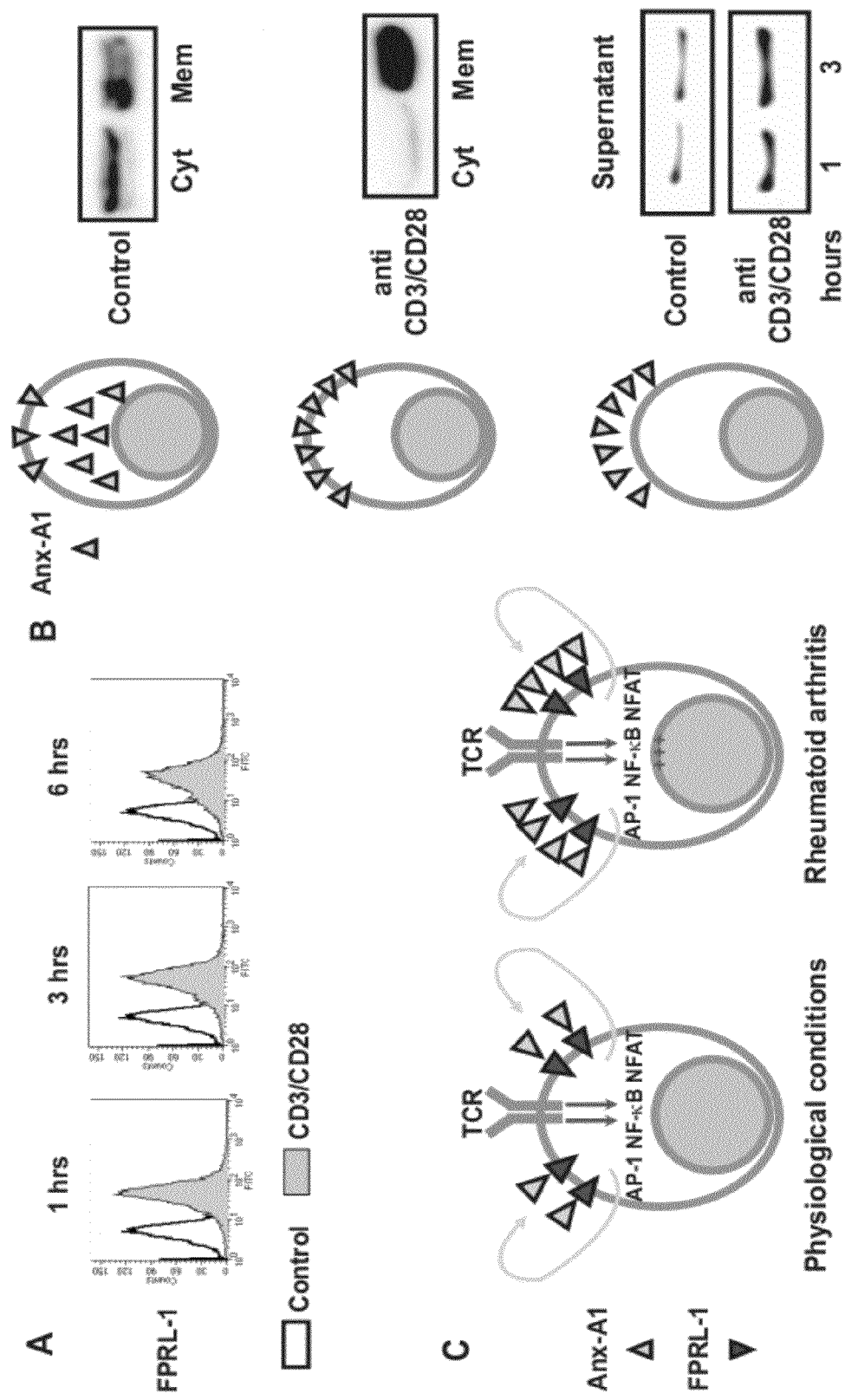

FIG. 6A shows FACS analysis of FPRL-1 expression in T cells stimulated with anti-CD3/CD28 (5.0 μg/ml) for the indicated times. FIG. 6B shows the cellular localization of Anx-A1 in T cells before (Control) or after stimulation with anti- CD3/CD28 (5.0 µg/ml). FIG. 6C is a schematic representation of the role of the Anx-A1/FPRL-1 system in T cells.

Figure 7:
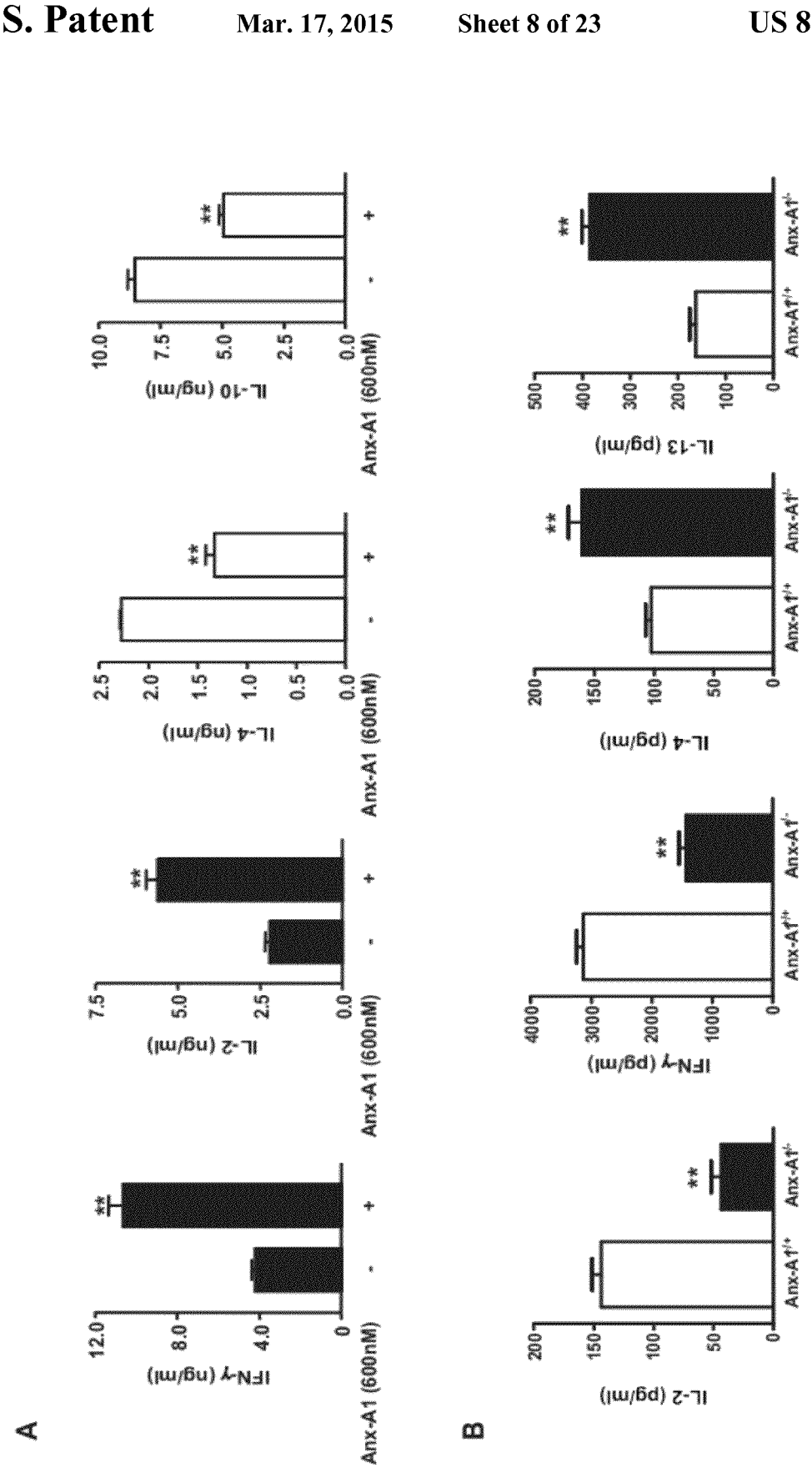

FIG. 7 shows that exogenous and endogenous Anx-A1 modulates Th1/Th2 differentiation. FIG. 7A shows the results when naïve lymph node T cells were differentiated in vitro in Th1 (black bars) or Th2 (white bars) conditions in presence or absence of hrAnx-A1 and then restimulated with plate-bound anti-CD3 to measure Th1 or Th2 cytokine production. FIG. 7B shows the results when naïve lymph node T cells from Anx-A1$^{+/+}$ or Anx-A1$^{-/-}$ mice were differentiated in vitro in Th1 (first and second column graphs from the left) or Th2 (third and fourth column graphs from the left) conditions and then restimulated with plate-bound anti-CD3 to measure Th1 or Th2 cytokine production.

Figure 8:
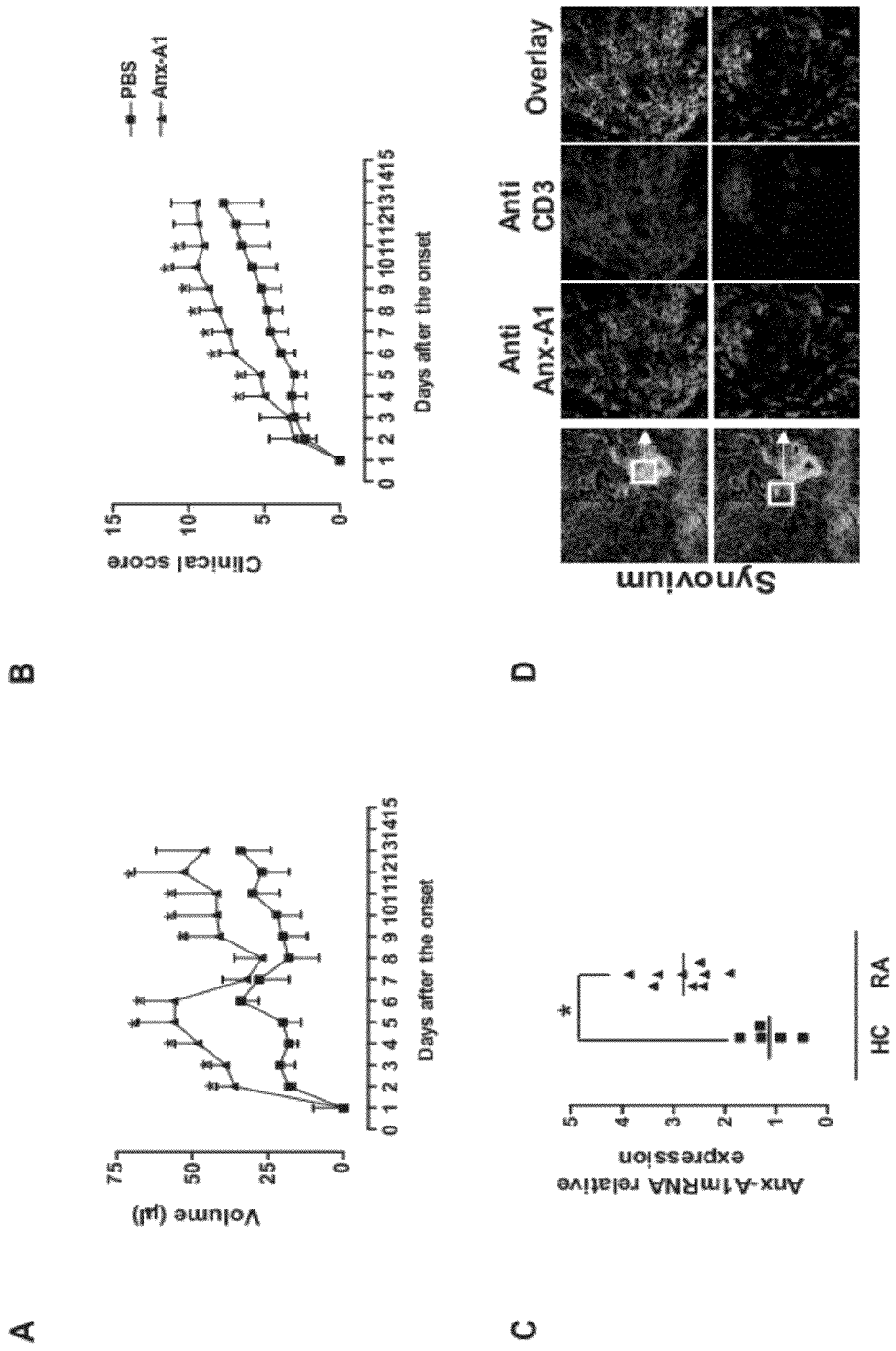

FIG. 8 shows paw volume (FIG. 8A) and clinical score (FIG. 8B) of DBA mice treated with PBS or hrAnx-A1 for 12 days during the immunization phase of the collagen-induced arthritis (CIA) model. FIG. 8C is an analysis of Anx-A1 expression in CD4+ cells of healthy control volunteers (HC) or rheumatoid arthritis (RA) patients. FIG. 8D shows an immunohistochemical analysis of Anx-A1 expression in synovial tissue from RA patients.

Figure 9:
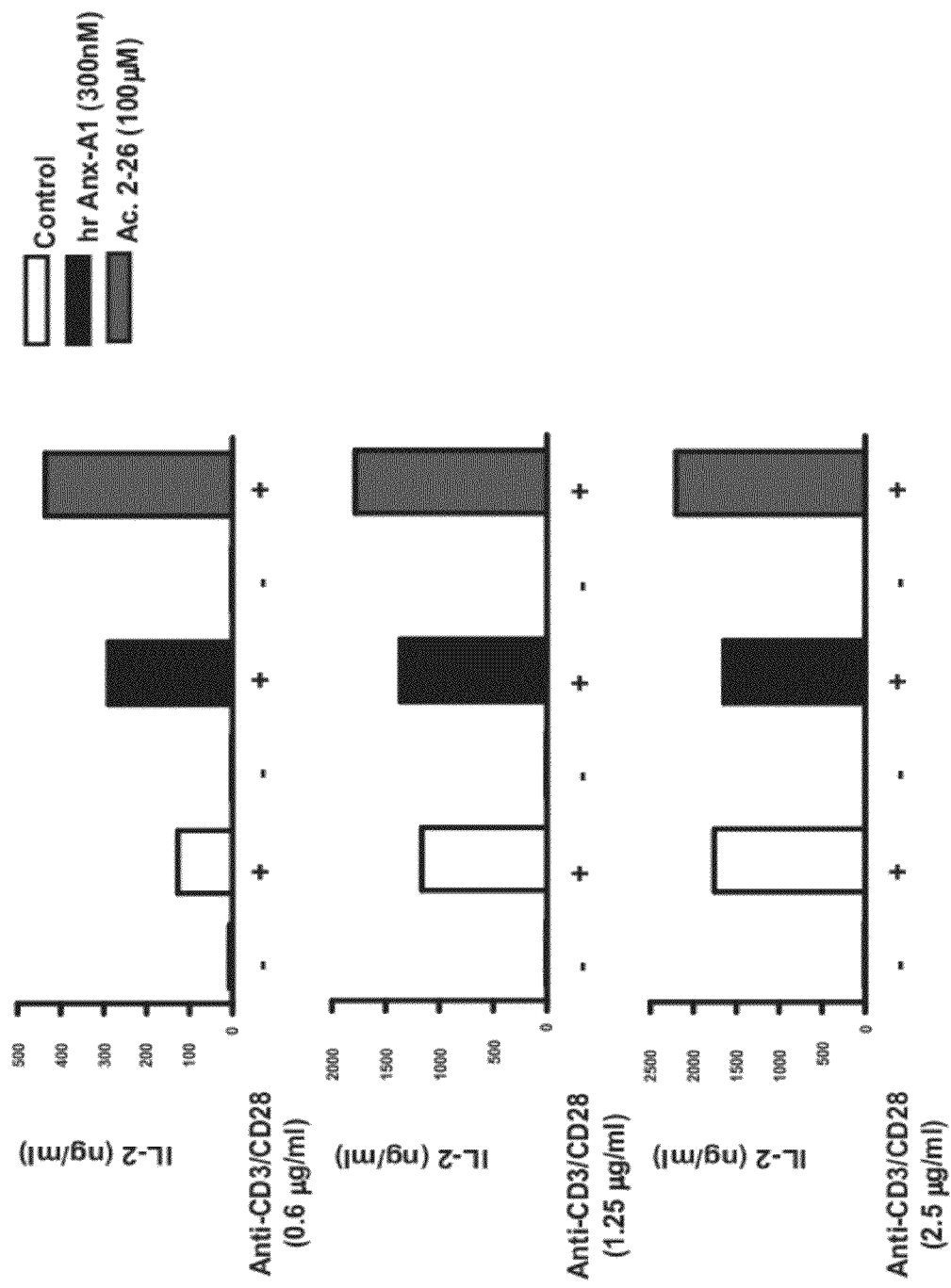

FIG. 9 shows the effects of full length hrAnx-A1 and the N-terminal peptide Ac 2-26 on T cell activation.

FIG. 10 shows the expression of Anx-A1 in human atherosclerotic plaques. Immunohistochemical analysis of Anx-A1 expression with mouse monoclonal anti-human Anx-A1 antibody 1B (FIG. 10A) or with nonimmune IgG (FIG. 10B) in carotid atherosclerotic plaques removed from patients during carotid endarteretomy surgery. Photographs are from a single patient and representative of six different patients with similar conditions.

Figure 11:
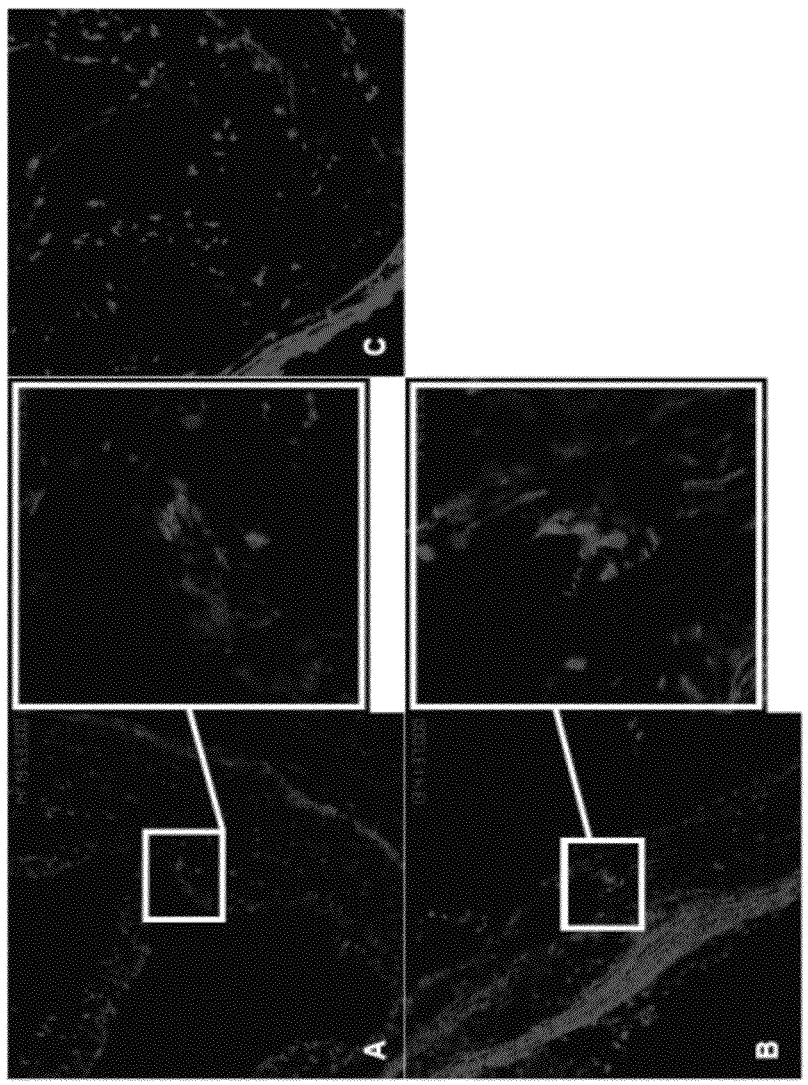

FIG. 11 shows expression of Anx-A1 in murine atherosclerotic plaques. FIG. 11 shows immunofluorescence visualization of Anx-A1 in ApoE$^{-/-}$ mice aortic sinus (FIG. 11A and FIG. 11B) and brachiocefalic artery (FIG. 11C). Sections were stained with Dapi to locate nuclei. Results illustrated are from a single experiment and are representative of three separate experiments. Original magnification: ×200 (FIG. 11A and FIG. 11B), ×400 (FIG. 11C).

Figure 12:
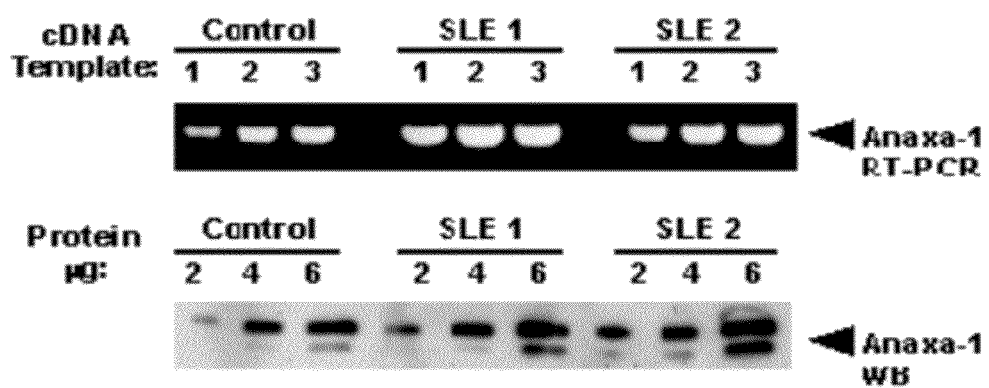

FIG. 12 shows expression of Annexin-1 in Systemic Lupus Erythematosus (SLE) patients. RT-PCR (upper panel) and Western Blot (lower panel) analysis of Anx-A1 expression in T cells from healthy (Control) or Systemic Lupus Erythematosus (SLE) patients. The numbers in the figure indicate the volume (µl) of cDNA or the amount (µg) of proteins obtained from the same number ($2\times10^6$) of T cells collected from healthy (Control) or Systemic Lupus Erythematosus (SLE) patients.

Figure 13:
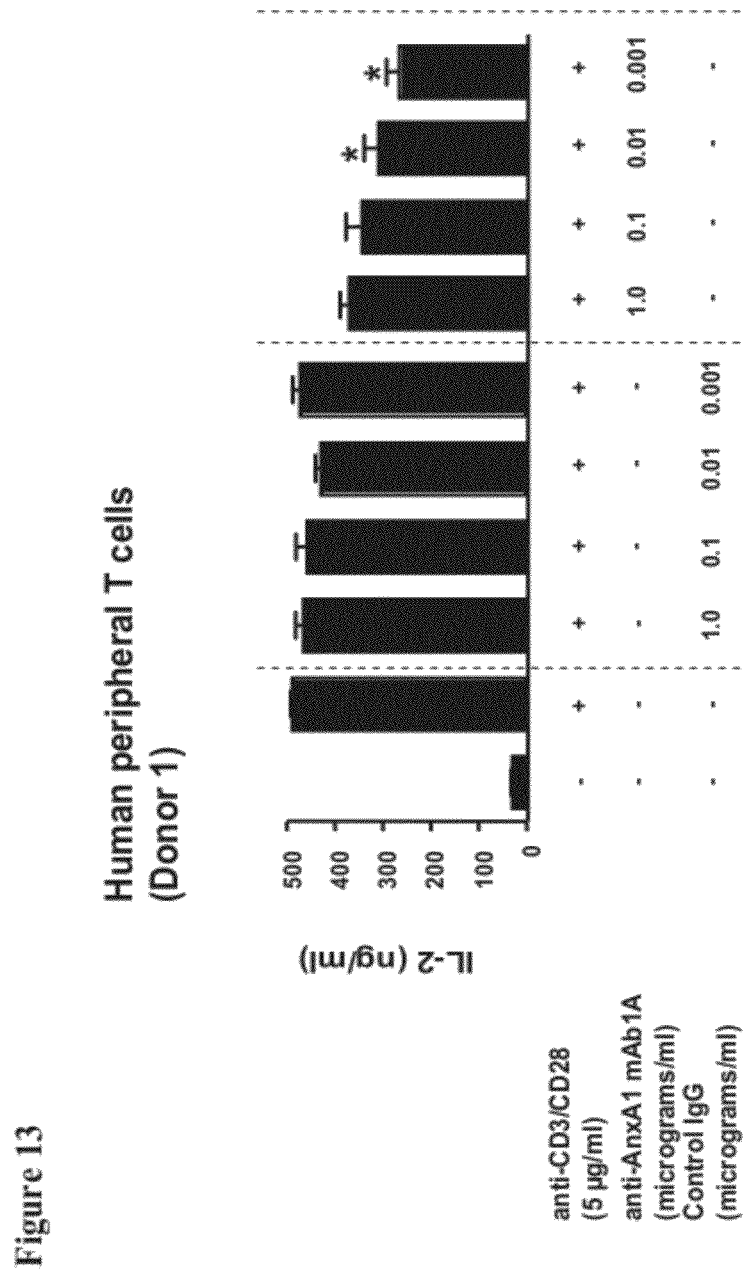

FIG. 13 shows inhibition of activation of the T cell receptor (TCR), measured in terms of interleukin-2 (IL-2) production, in human peripheral T cells from one donor incubated with a neutralising monoclonal antibody raised against human recombinant annexin-1 (anti-AnxA1 mAb1A).

Figure 14:
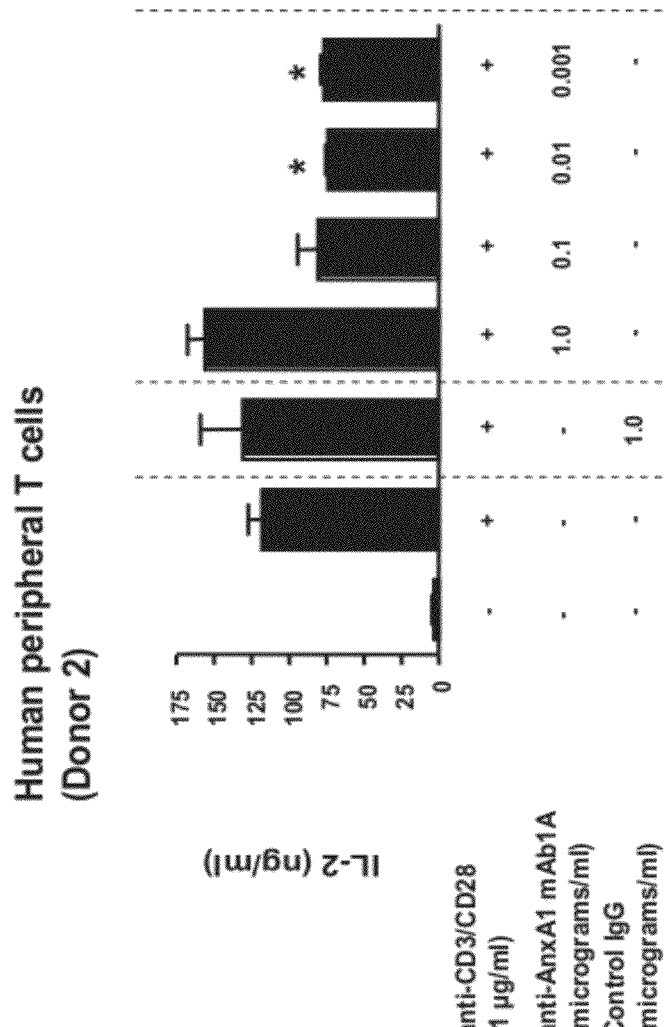

FIG. 14 shows inhibition of activation of the T cell receptor (TCR), measured in terms of interleukin-2 (IL-2) production, in human peripheral T cells from a different donor incubated with a neutralising monoclonal antibody raised against human recombinant annexin-1 (anti-AnxA1 mAb1A).

Figure 15:
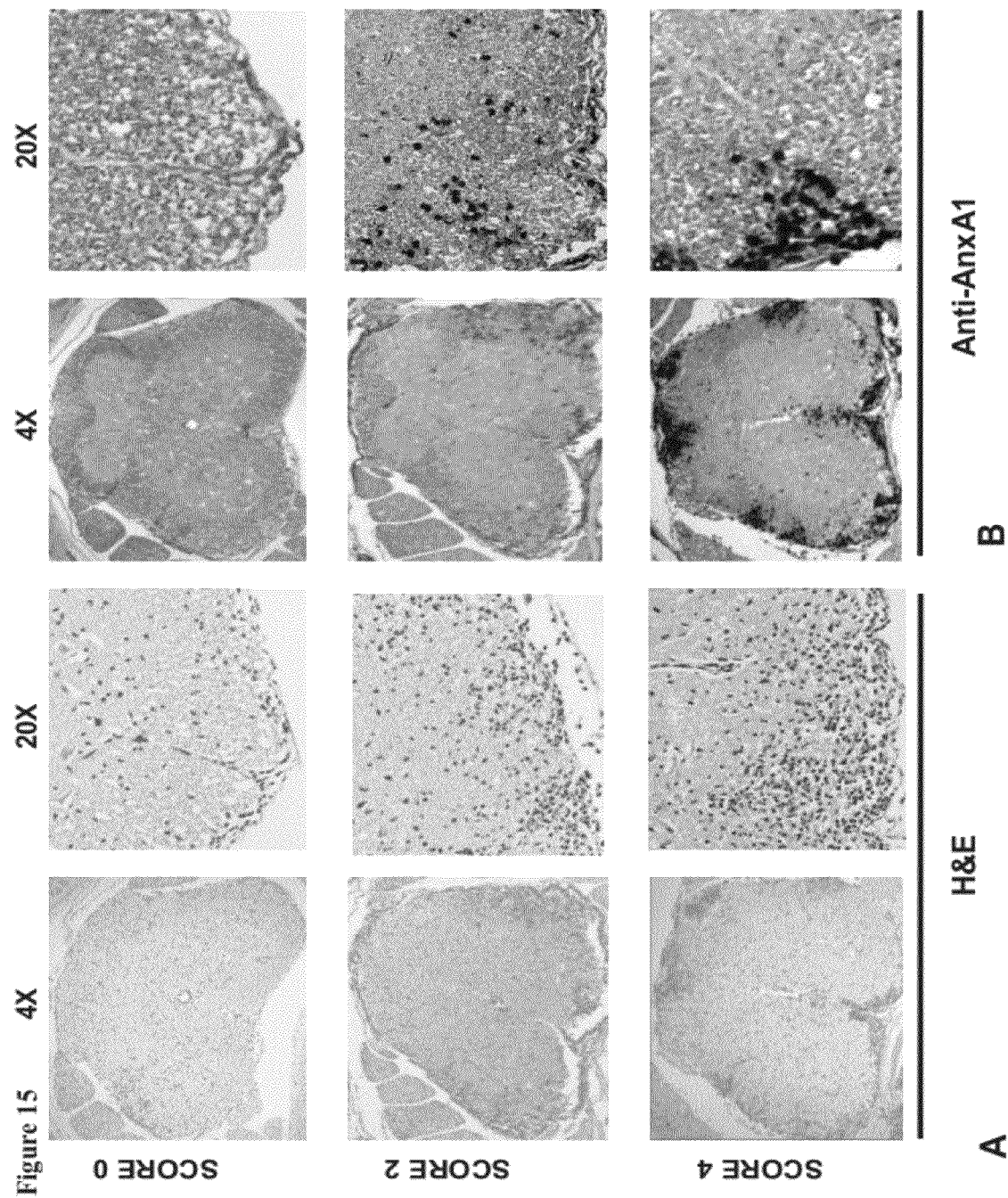

FIG. 15 shows spinal cord sections from C57BL/6 mice immunized with MOG$_{35-55}$ and CFA and from which spinal cords removed at day 12 (score 0), day 18 (score 2) and day 20 (score 4). The sections were stained with hematoxylin and eosin (H&E, FIG. 15A) or anti-AnxA1 (FIG. 15B). For each staining, the right panels (20×) show a higher magnification of an area of the left panels (4×). Results representative of 3 experiments.

Figure 16:
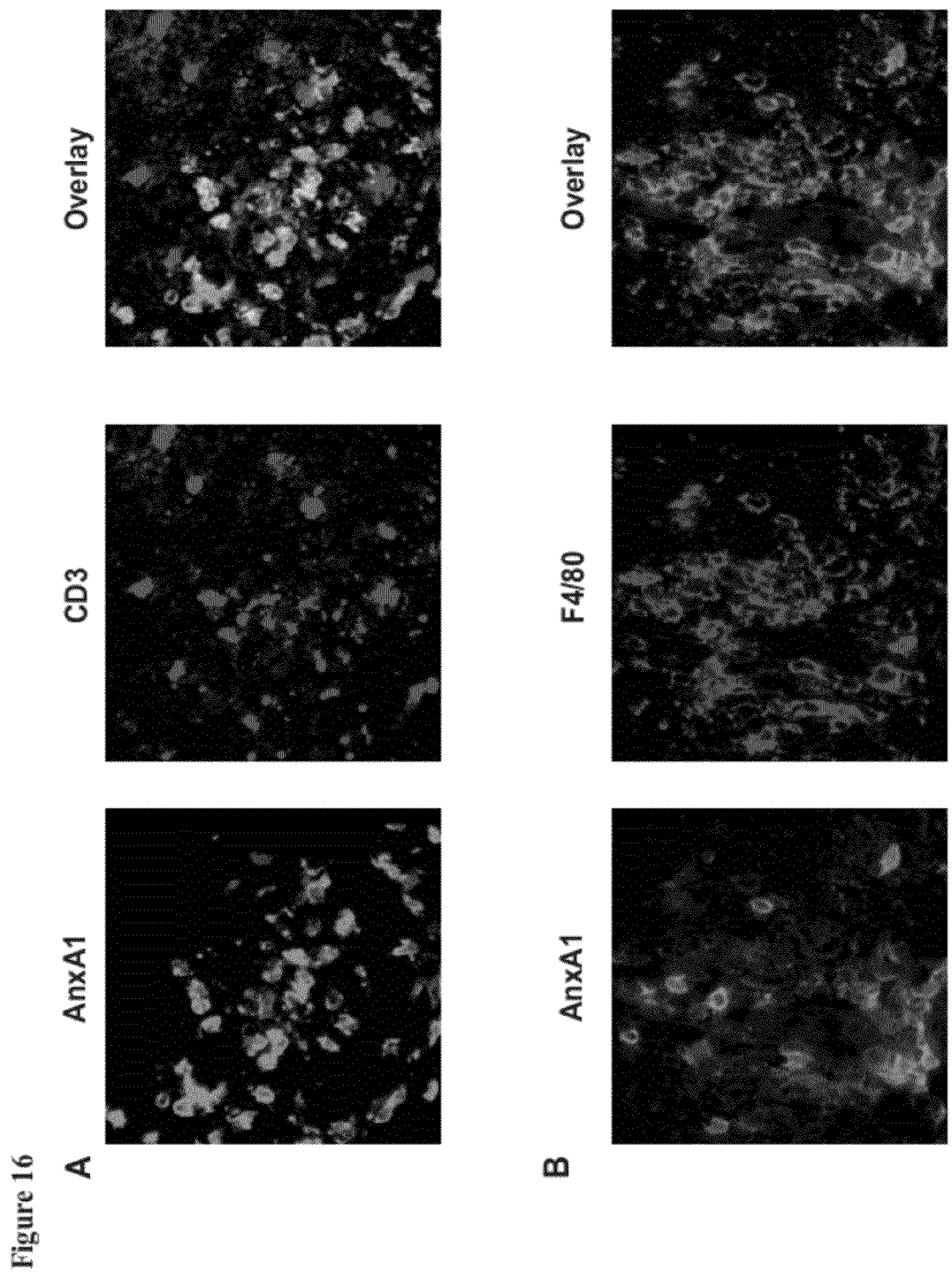

FIG. 16 shows spinal cord sections from C57BL/6 mice immunized with MOG$_{35-55}$ and CFA and from which spinal cords removed at day 20 (score 4). The sections were stained with anti-AnxA1 and anti-CD3 (A) or anti-F4/80 (B). The right panels show an overlay of the two single stainings on the right. Results representative of 3 experiments.

Figure 17:
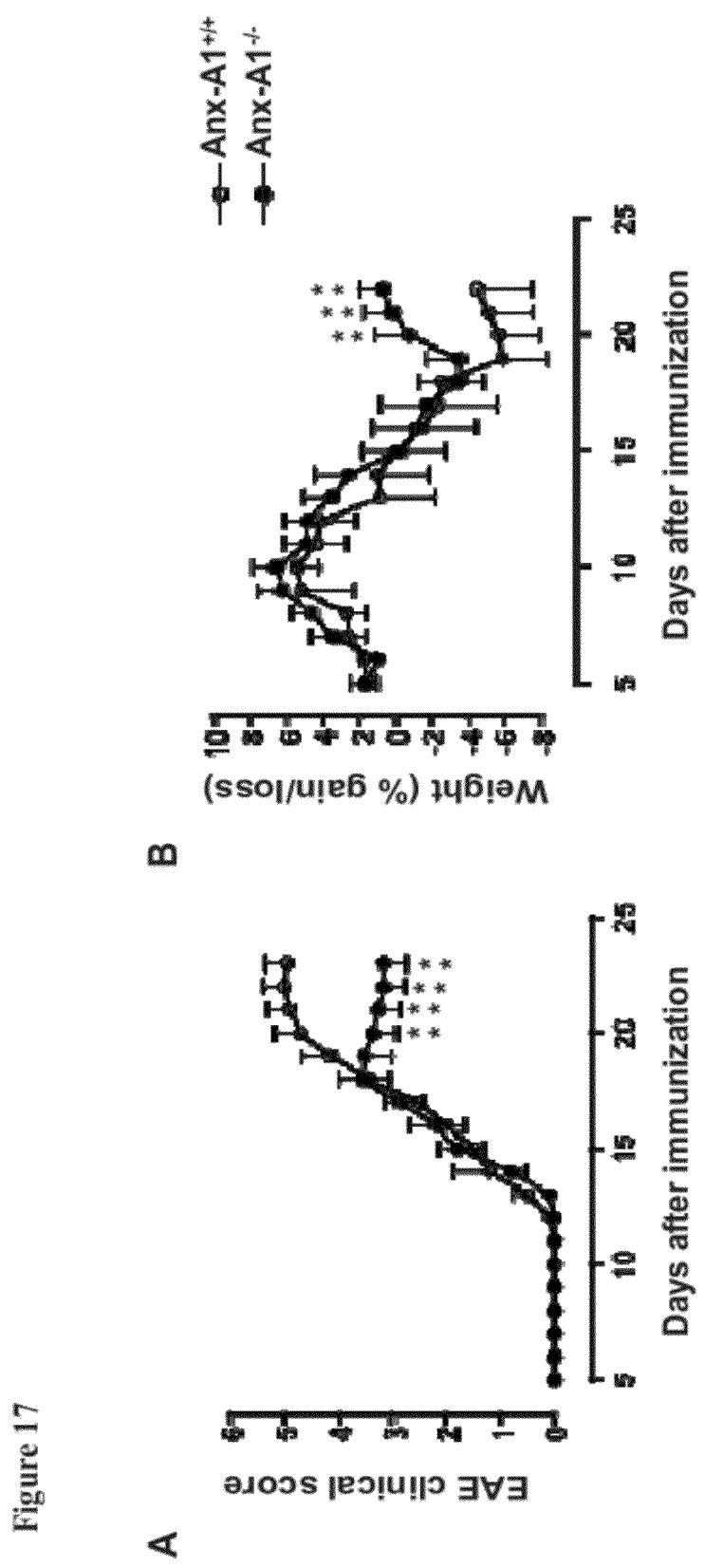

FIG. 17 shows the results from a study in which C57BL/6 mice were immunized with MOG$_{35-55}$ and CFA and monitored daily for signs and symptoms of EAE (A) or weight gain/loss (B) for 23 days. Results are means±SEM (n=10/group). **p<0.01, representative of 3 experiments.

Figure 18:
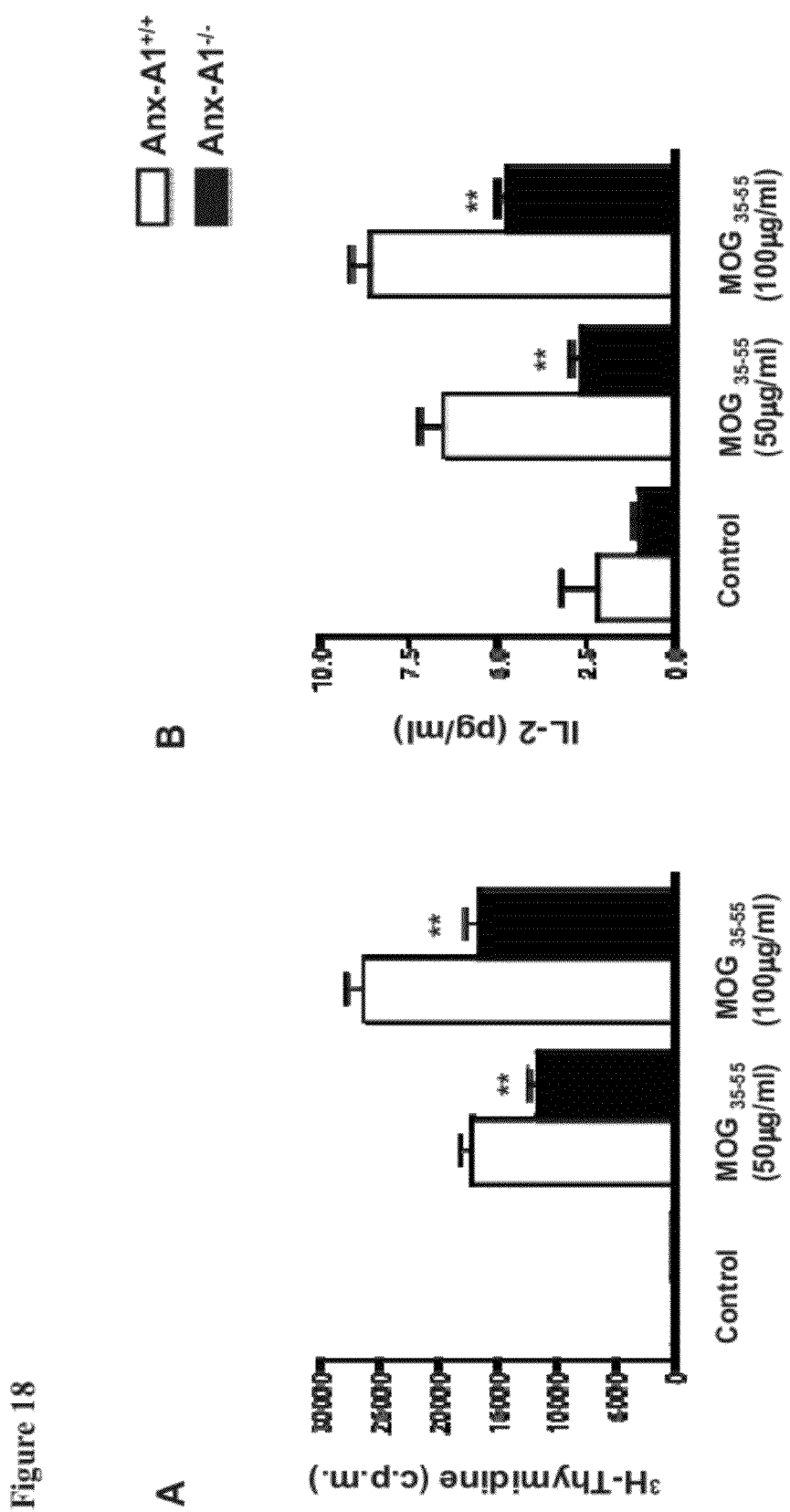

FIG. 18 shows the incorporation of $^3$H-Thymidine (A) and the production of IL-2 (B) of lymph node cells obtained from AnxA1$^{+/+}$ and AnxA1$^{-/-}$ mice immunized with MOG$_{35-55}$ and CFA and sacrificed after 14 days. Cells were stimulated with MOG$_{35-55}$ for 48 hours and pulsed with 1 µCi $^3$H-Thymidine for 12 hours. Cell supernatants were used to measure IL-2 production. Results are means±SEM (n=4/group). *p<0.05, **p<0.01, representative of 3 experiments.

Figure 19:
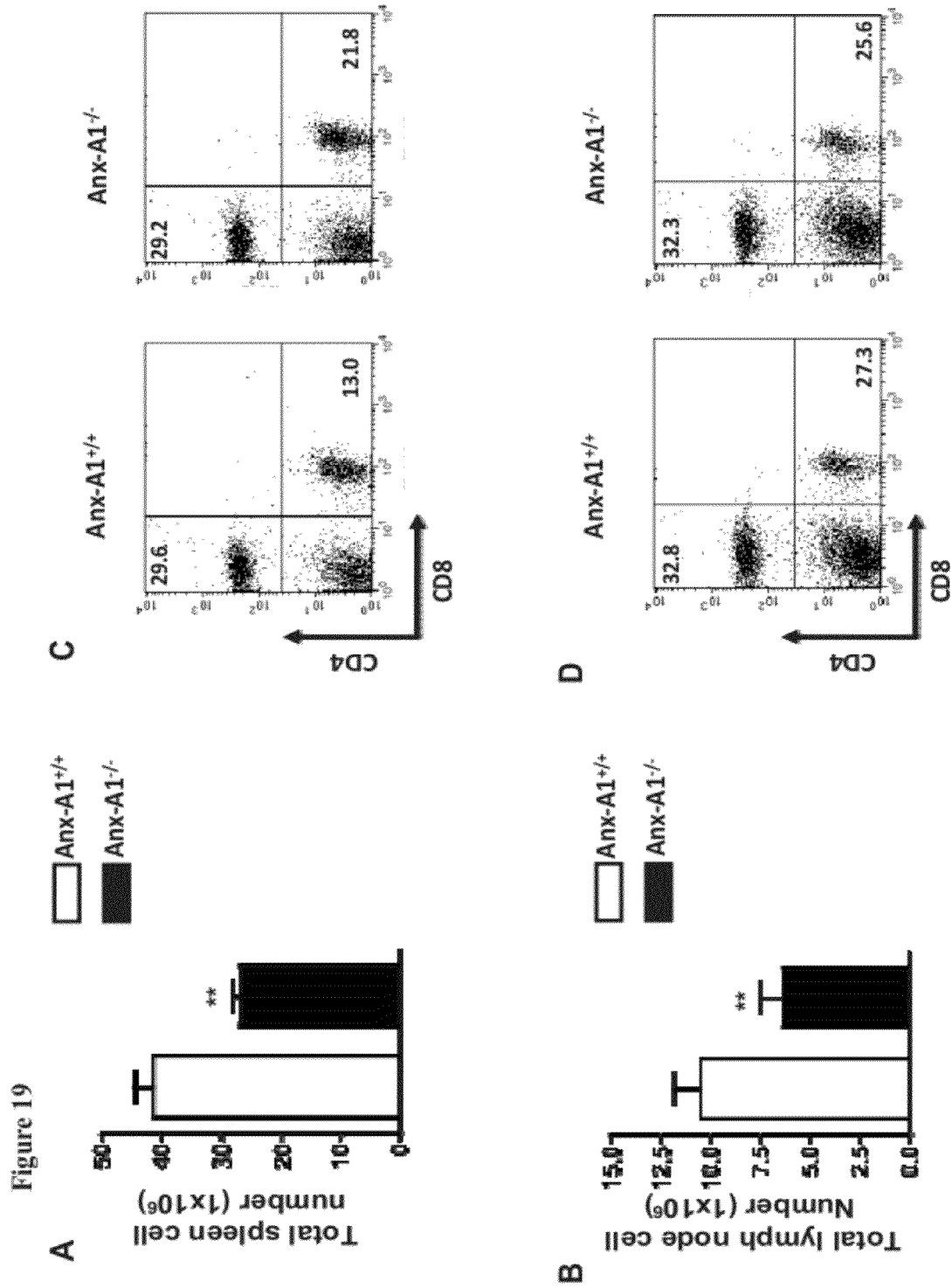

FIG. 19 shows the total cell number of spleen (A) and lymph node (B) cells obtained from AnxA1$^{+/+}$ and AnxA1$^{-/-}$ mice immunized with MOG$_{35-55}$ and CFA and sacrificed after 14 days. C and D show the cytofluorimetric analysis of lymph node cells with anti-CD4 FITC and anti-CD8 PE. Results are means±SEM (n=10/group). **p<0.01, representative of 3 experiments.

Figure 20:
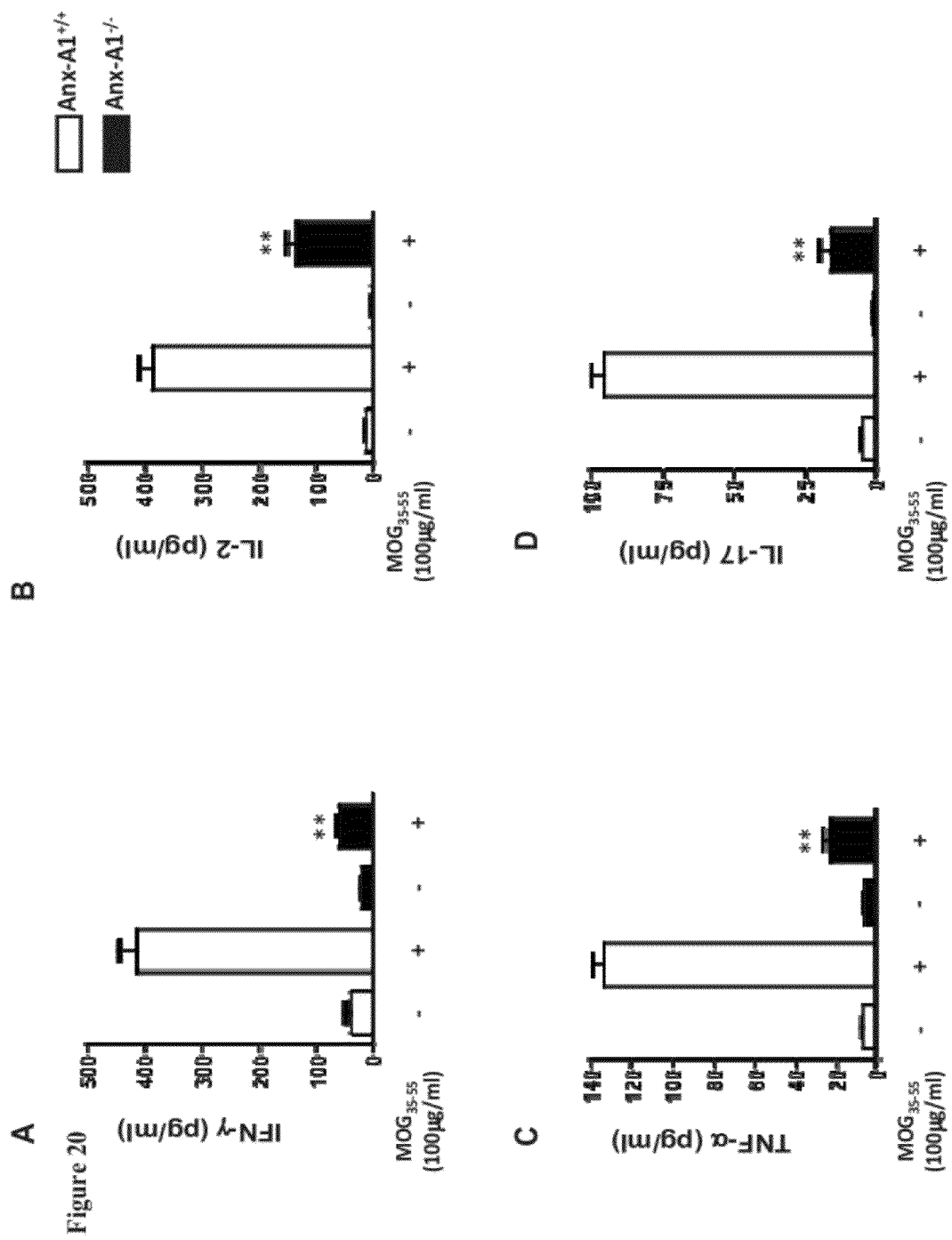

FIG. 20 shows levels of (A) IFN-γ, (B) IL-2, (C) TNF-α and (D) IL-17 in the cell supernatants of lymph node cells obtained from AnxA1$^{+/+}$ and AnxA1$^{-/-}$ mice immunized with MOG$_{35-55}$ and CFA and sacrificed after 14 days. Cells were stimulated with the indicated concentration of MOG$_{35-55}$ for 4 days and the supernatants used for cytokine ELISA. Results are means±SEM (n=4/group). *p<0.05, **p<0.01, representative of 3 experiments.

Figure 21:
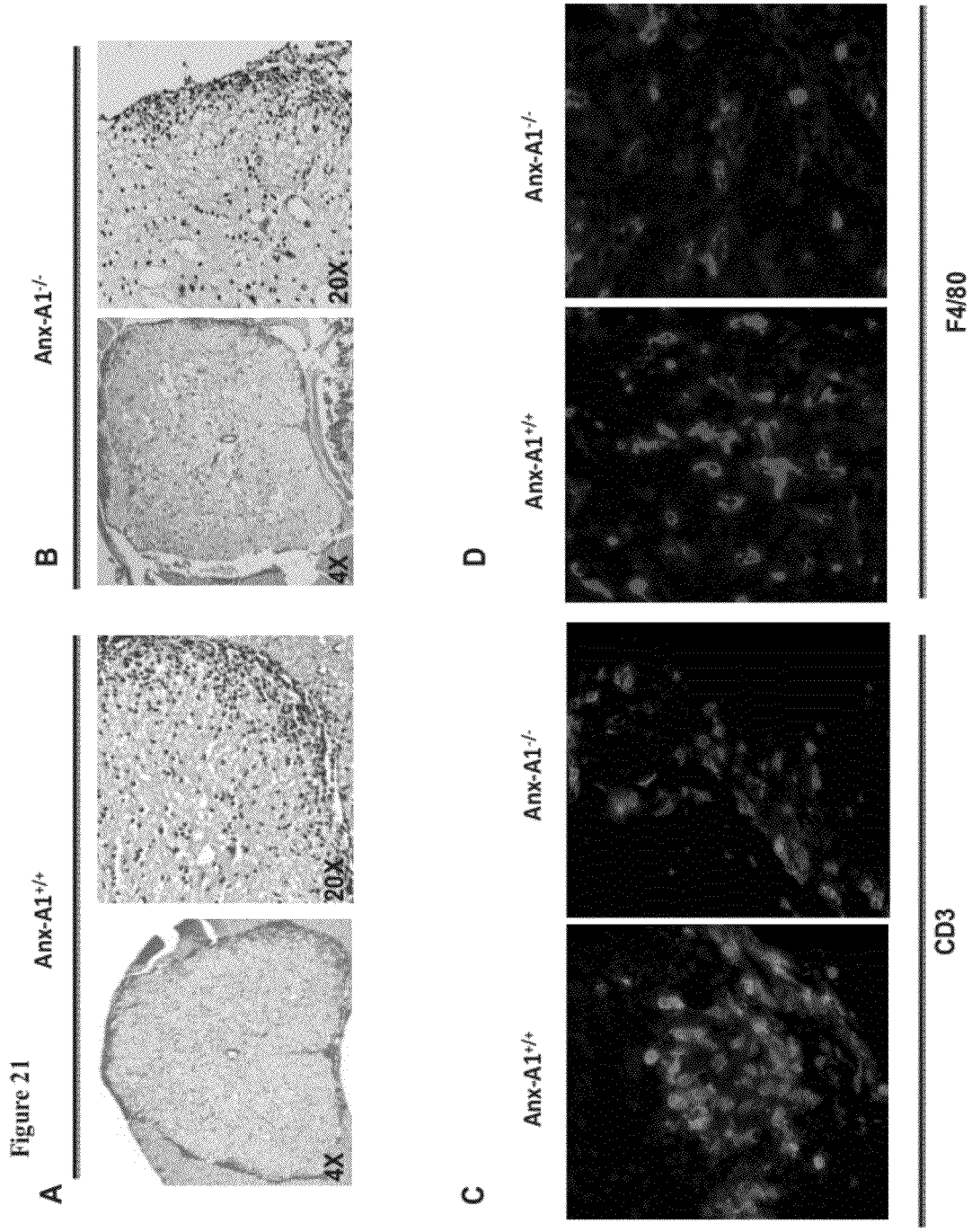

FIG. 21 shows haematoxylin-eosin staining of spinal cord sections obtained from AnxA1$^{+/+}$ (A) and AnxA1$^{-/-}$ (B) mice immunized with MOG$_{35-55}$ and CFA and sacrificed after 22 days. For each staining, the right panels (20×) show a higher magnification of an area of the left panels (4×). Consecutive sections were stained with anti-CD3 (C) or anti-F4/80 (D). Pictures are representative of three separate experiments with similar results.

Figure 22:
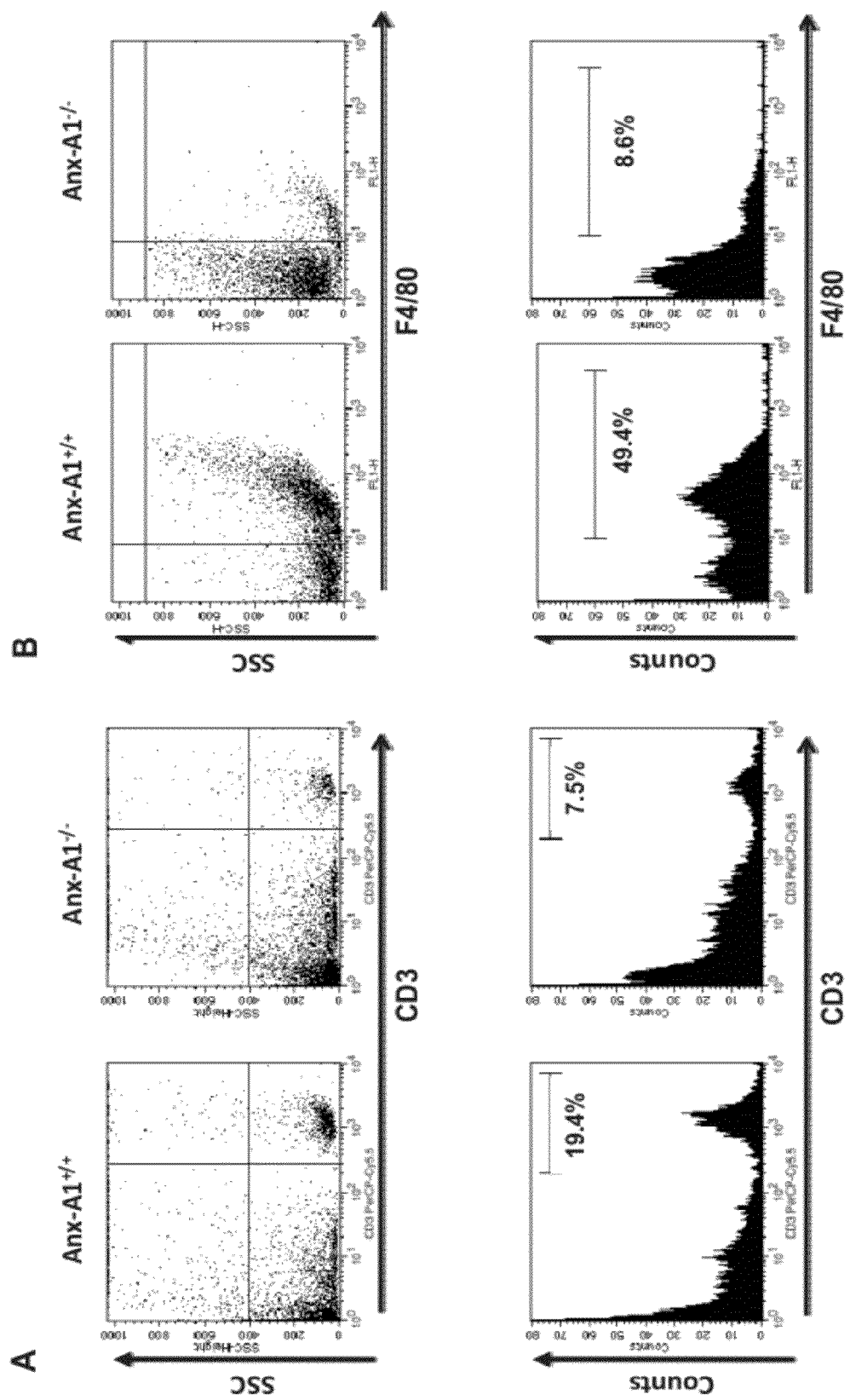

FIG. 22 shows FACS analysis of CD3 (A) and F4/80 (B) positive mononuclear cells recovered by Percoll gradient of spinal cord homogenates obtained from AnxA1$^{+/+}$ and AnxA1$^{-/-}$ mice immunized with MOG$_{35-55}$ and CFA and sacrificed after 14 days. The dot plots and histograms are from a single mouse and representative of 2 experiments with n=4 mice. The numbers in the histograms indicate the percentage of CD3$^+$ and F4/80$^+$ cells.

EXAMPLES 1 TO 10

Materials and Methods

Reagents

Anti-mouse CD3 (clone 145-2C11), anti-mouse CD28 (clone 37.51), anti-human CD3 (clone OKT3), anti-human CD28 (clone CD28.2), PE-conjugated anti-CD69 (clone H1.2F3), FITC-conjugated anti-CD25 (clone PC61.5), murine IL-2, IL-4, IFN-γ, IL-12, anti-IL-4 (clone 11B11), and anti-IFN-γ (clone XMG1.2) were purchased from eBioscience (Wembley, United Kingdom). Endotoxin-free human recombinant Anx-A1 (hrAnx-A1) was prepared as described.

In some experiments, we used denatured hrAnx-A1 (heat-inactivated at 95° C. for 5 minutes) as positive control. Unless otherwise specified, all the other reagents were from Sigma-Aldrich (St Louis, Mo.).

Mice

BALB/C, C57/BL6 and DBA/1 male mice were obtained from Charles River Laboratories (Wilmington, Mass.). Annexin 1 null mice on BALB/C were generated in our lab and bred in pathogen-free conditions in our animal facilities. All mice used in these studies were between 6 and 8 weeks old. Animal work was performed according to United Kingdom Home Office regulations (Guidance on the Operation of Animals, Scientific Procedures Act 1986) and along the directives of the European Union.

Isolation of Cells from Patients

Peripheral blood mononuclear cells (PBMCs) were prepared from peripheral blood using Ficoll density centrifugation (Ficoll-Paque Plus; Amersham Biosciences, Freiburg, Germany). $CD4^+$ cells were selected from peripheral blood using positive selection. Briefly, peripheral blood was subjected to Ficoll density centrifugation (Ficoll-Paque Plus; Amersham Biosciences). Adherent cells were removed from the mononuclear cells by adherence to serum-coated plastic. Nonadherent cells were incubated with mouse anti-human CD4 antibody (RFT4), washed in buffer (phosphate-buffered saline [PBS], 0.5% bovine serum albumin [BSA], 2 mM EDTA pH 7.2) and incubated with goat antimouse antibody conjugated to a magnetic bead (Miltenyi Biotec, Auburn, Calif.). Cells were run through a MACS column (Miltenyi Biotec) and $CD4^+$ cells were collected. The purity of the cells was assessed by flow cytometry. The median percentage of $CD3^+$ $CD4^+$ cells following the 10 depletions was 98% (range, 97%-99.3%). Remaining cells were resuspended in lysis buffer (Ambion, Huntingdon, United Kingdom).

Cell Culture

Primary murine T cells were prepared from lymph nodes by negative selection. Briefly, axillary, inguinal, and mesenteric lymph nodes were teased apart to make a single cell suspension, then washed and layered over Ficoll. The buffy coat was washed 2 times and then incubated with the antibody mix and the magnetic beads following the manufacturer's instructions (mouse T-cell negative isolation kit; Dynal, Bromborough, United Kingdom). In some experiments, cells were further purified to obtain naive $CD62L^+$ $CD4^+$ T cells by using the Miltenyi Biotec $CD62L^+$ $CD4^+$ T-cell isolation kit. Th0 conditions were created by T cells for 4 days in 6-well plates precoated with anti-CD3 (5 µg/mL) and anti-CD28 (5 µg/mL) in complete RPMI medium (10% fetal calf serum [FCS], 2 mM L-glutamine, and 100 units $mL^{-1}$ gentamycin) containing murine IL-2 (20 U/mL). Th1 conditions were created with murine IL-12 (3.4 ng/mL; eBioscience), IL-2 (20 U/mL; eBioscience), and anti-IL4 (clone 11B11; 2 µg/mL). Th2 conditions were created with IL-4 (3000 U/mL; Peprotech, Rocky Hill, N.J.), IL-2 (20 U/mL), and anti-IFN-γ (clone XMG1.2; 2 µg/mL). Jurkat cells were obtained from ATCC (Manassas, Va.) and were cultured in complete RPMI medium.

Flow Cytometric Analysis

Purified lymph node T cells were pretreated with human recombinant Anx-A1 for 2 hours at 37° C. in Eppendorf tubes and then stimulated with plate-bound anti-CD3 and anti-CD28 as indicated in the figures. After 16 hours, the cells were stained with PE-conjugated anti-CD69 (clone H1.2F3) and FITC-conjugated anti-CD25 (clone PC61.5) diluted in FACS buffer (PBS containing 1% FCS and 0.02% $NaN_2$). Intact cells were gated by using forward and side scatter and were analyzed with the CellQuest program (Becton Dickinson, Franklin Lakes, N.J.) on a FACScan flow cytometer. To analyze FPRL-1 expression, human peripheral blood T cells were stimulated with plate-bound anti-CD3 and anti-CD28 for different times and thereafter stained with mouse anti-human FPRL-1 (clone 6C7-3-A; 5 µg/mL), followed by FITC-conjugated antibody.

Cell Proliferation Assay

Purified lymph node T cells ($10^5$ cells/mL) were incubated with medium alone or with different concentrations of hrAnx-A1 for 2 hours at 37° C. in Eppendorf tubes. Thereafter, aliquots of 200-µL cell suspension were stimulated by plate-bound anti-CD3 and anti-CD28 for 24 hours in 96-well plates. After 18 hours, cultures were pulsed for 8 hours with 1 µCi ($3.7 \times 10^4$ Bq) [$^3$H]-thymidine (Amersham Pharmacia Biotech, Piscataway, N.J.) and incorporated radioactivity was measured by automated scintillation counter (Packard Instruments, Pangbourne, United Kingdom).

Electromobility Shift Assays

Nuclear extracts were harvested from $3 \times 10^6$ to $5 \times 10^6$ cells according to previously described protocols. Nuclear extracts (3 µg to 5 µg) were incubated with 1 µg (for NFAT) or 2 µg (for NF-κB and AP-1) of poly (dI:dC) in 20 µL binding buffer with $^{32}P$ end-labeled, double-stranded oligonucleotide probes ($5 \times 10^5$ cpm), and fractionated on a 6% polyacrylamide gel (29:1 cross-linking ratio) in 0.5% TBE for 2.5 hours at 150 V. The NF-κB and AP-1 binding buffer (10×) contained 100 mM Tris-HCl, (pH 7.5), 500 mM NaCl, 10 mM EDTA, 50% glycerol, 10 mg/mL albumin, 30 mM GTP, 10 mM DTT. The NFAT binding buffer (10×) contained 100 mM Hepes (pH 7.9), 500 mM KCl, 1 mM EDTA, 1 mM EGTA, 50% glycerol, 5 mg/mL albumin, 1% Nonidet P-40, 10 mM DTT. The NF-κB and AP-1 double-stranded oligonucleotide probes were from Promega and the NFAT was from Santa Cruz Biotechnology (Santa Cruz, Calif.).

Western Blotting Analysis

Lymph node T cells were incubated as indicated in the figures. After incubation at 37° C. for various time periods, cells were lysed in ice-cold lysis buffer (1% NP-40, 20 mM Tris pH 7.5, 150 mM NaCl, 1 mM $MgCl_2$, 1 mM EGTA, 0.5 mM PMSF, 1 µM aprotinin, 1 µM leupeptin, 1 µM pepstatin, 50 mM NaF, 10 mM $Na_4P_2O_7$, and 1 mM $NaVO_4$, 1 mM β-glycerophosphate). The cell lysates were centrifuged at 13/226 g (13 000) rpm for 5 minutes at 4° C. and the supernatants were collected and subjected to electrophoresis on SDS-10% polyacrylamide gel. After transfer, the membranes were incubated overnight with antibodies diluted in Tris-buffered saline solution containing Tween-20 (TTBS: 0.13 M NaCl; 2.68 mM KCl; 0.019 M Tris-HCl; 0.001% vol/vol Tween-20; pH 7.4) with 5% nonfat dry milk at 4° C. For the experiments with anti-pERK1/2 and anti-Akt, the TTBS buffer was supplemented with 50 mM NaF and bovine serum albumin (5%) was used instead of milk. For each condition, extract equivalents obtained from the same number of cells were used. Immunoblotting and visualization of proteins by enhanced chemiluminescence (ECL; Amersham Pharmacia Biotech) were performed according to the manufacturer's instructions. To obtain cytosolic and membrane fractions, cells were first collected and washed in ice-cold PBS and then centrifuged briefly for 2 minutes at 300 g. The resultant cell pellet was lysed in lysis buffer (20 mM Tris-HCl, pH 7.5; protease inhibitors as listed in the lysis buffer) and passed through a 25-gauge needle at least 5 times to ensure sufficient lysis. The suspension was then centrifuged for 2 minutes at 300 g, the supernatant collected, and centrifuged again for 45 minutes at 800 g (4° C.). At this stage the supernatant (cytosolic fraction) was collected and the pellet (membrane fraction) resuspended in lysis buffer containing 1% (vol/vol) Triton X-100. All fractions were kept on ice throughout the experiments.

Cytokine ELISA

For Th1/Th2 cytokine production analysis, Th0/Th1/Th2 cells ($10^6$/mL) obtained after 4-day differentiation in skewing conditions and 1 day of resting in complete RPMI medium, were stimulated with plate-bound anti-CD3 (5 µg/mL) for 8 h in 24-well plates. Culture supernatants were collected and analyzed for IFN-γ, IL-2, IL-4 and IL-10 content by using Th1/Th2 panel ELISA kit (eBioscience). The IL-13 ELISA kit was also purchased from eBioscience.

Example 1

Effect of Human Recombinant Annexin-1 (hrAnx-A1) on T Cell Activation

Figure 3:
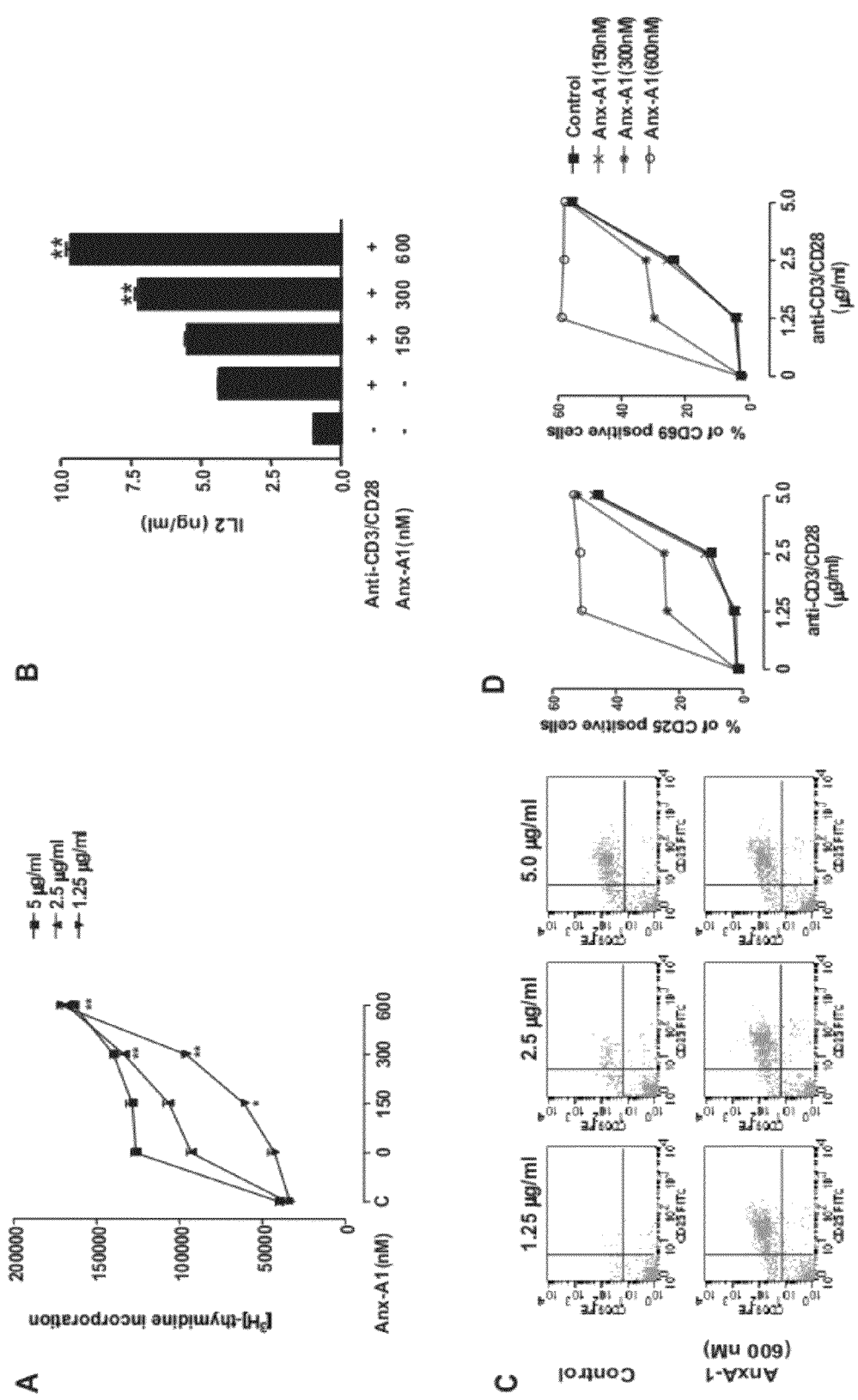
FIG. 3 shows the effect of human recombinant Annexin-1 (hrAnx-A1) on T cell activation. Pre-treatment of murine naïve CD4+ primary cells with hrAnx-A1 followed by activation with different concentrations of anti-CD3/CD28 augmented cell proliferation (FIG. 3A), IL-2 production (FIG. 3B) and cell surface expression of CD25 and CD69 (FIGS. 3C and 3D).

Murine naïve lymph nodes T cells were stimulated with 5.0 (■), 2.5 (▲) and 1.25 (▼) µg/ml of anti-CD3/CD28 in the absence of or in the presence of different concentrations of hrAnx-A1 for 24 hrs and were then pulsed with $^3$H-thymidine to measure proliferation. The results are shown in FIG. 3A.

FIG. 3B shows IL-2 production from primary murine naïve lymph node T cells stimulated with anti-CD3/CD28 (1.25 µg/ml) in the absence of or in the presence of different concentrations of hrAnx-A1 for 24 hrs.

Murine naïve lymph node T cells were stimulated with anti-CD3/CD28 at a concentration of 1.25 µg/ml (left column), 2.5 µg/ml (middle column) and 5.0 µg/ml (right column), in the absence of (upper panels) or in the presence of (lower panels) hrAnx-A1 (600 nM) for 12 hrs and then analyzed for CD25 and CD69 expression by FACS. The results are shown in FIG. 3C.

In FIG. 3D, murine naïve lymph node T cells were stimulated with the indicated concentration of anti-CD3/CD28 in the presence of 150 (X), 300 (✳) and 600 (○) nM of hrAnx-A1 for 12 hours and then analysed for CD25 (left graph) and CD69 (right graph) expression by FACS.

In all of the experiments values are mean±S.E. of n=3-4 mice. *P<0.05; **P<0.01.

The results show that pre-treatment of murine naïve CD4+ primary cells with hrAnx-A1 followed by activation with different concentrations of anti-CD3/CD28 augmented cell proliferation (FIG. 3A), IL-2 production (FIG. 3B) and cell surface expression of CD25 and CD69 (FIGS. 3C and D).

Example 2

Endogenous Anx-A1 Modulates T Cell Proliferation

Figure 4:
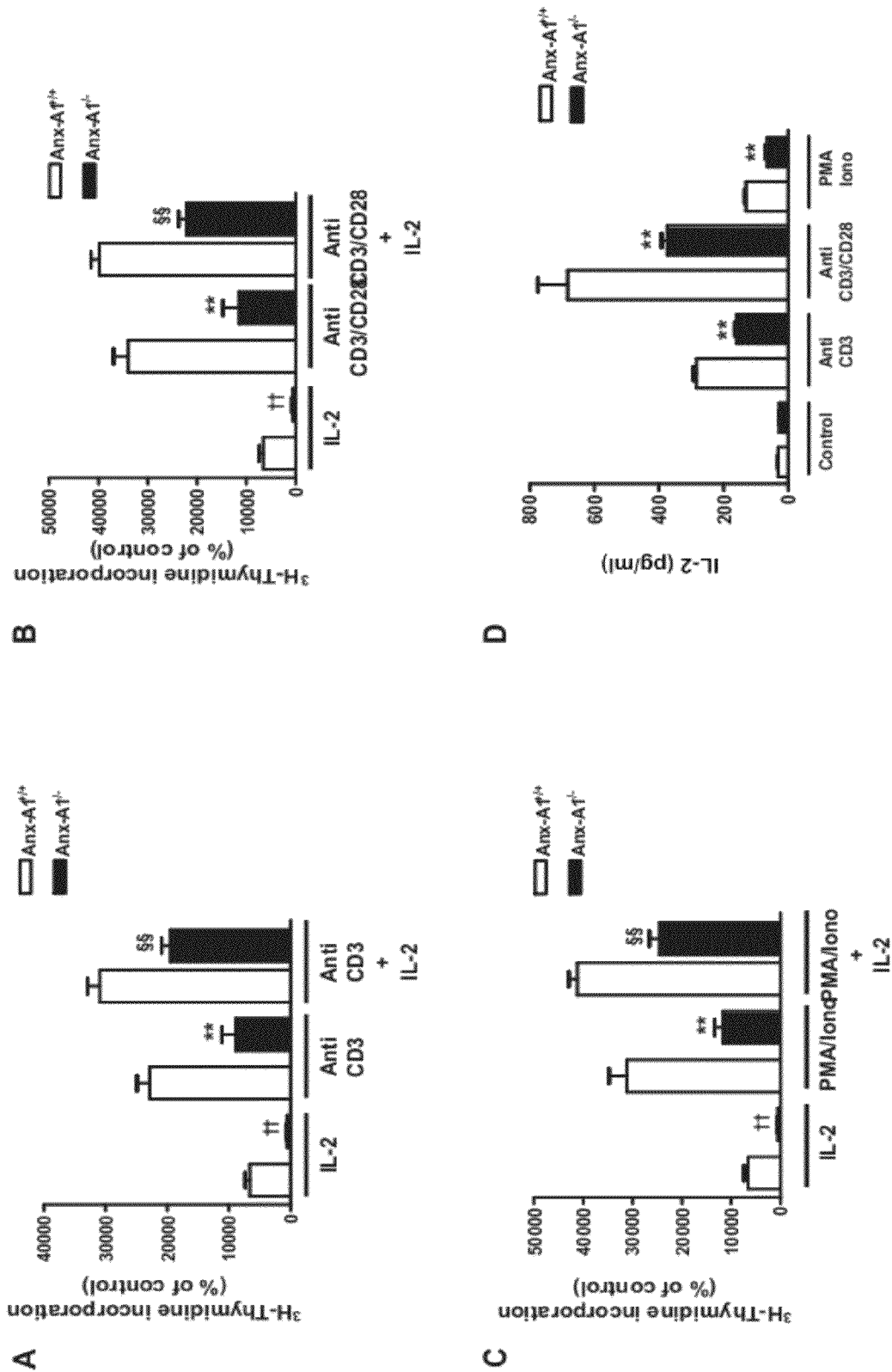
FIG. 4 shows that endogenous Anx-A1 modulates T cell proliferation. Stimulation of Anx-A1$^{+/+}$ or Anx-A1$^{-/-}$ T cells with anti-CD3, anti-CD3/CD28 or PMA/Ionomycin showed a decrease rate of $^3$H-thymidine incorporation (FIGS. 4A, 4B and 4C, respectively) and IL-2 production (FIG. 4D) in the Anx-A1 deficient T cells compared to control unstimulated T cells.

FIG. 4 shows that: (A) anti-CD3 (5.0 µg/ml) (B) anti-CD3/CD28 (5.0 µg/ml) or (C) PMA (20 ng/ml) and Ionomycin (2 ng/ml) induced proliferation of wild type and Anx-A1 deficient T cells, expressed as a percentage of $^3$H-thymidine incorporation compared to control unstimulated T cells. In some experiments, cells were also activated in presence of mouse recombinant IL-2 (20 ng/ml). Values are mean±S.E. of n=4-5 ††P<0.01 vs IL-2 stimulated Anx-A1$^{+/+}$ cells; **P<0.01 vs anti-CD3 or anti-CD3/CD28 or PMA/Ionomycin stimulated Anx-A1$^{+/+}$ cells; §§P<0.01 vs anti-CD3 or anti-CD3/CD28 or PMA/Ionomycin stimulated Anx-A1$^{-/-}$ cells.

FIG. 4D shows IL-2 production from naïve lymph node T cells stimulated with anti-CD3, anti-CD3/CD28 (5.0 µg/ml) or PMA (20 ng/ml) and Ionomycin (2 ng/ml) for 24 h. Values are mean±S.E. of n=4-5 mice. **P<0.01.

The results show that stimulation of Anx-A1$^{+/+}$ or Anx-A1$^{-/-}$ T cells with anti-CD3, anti-CD3/CD28 or PMA/ionomycin showed a decrease rate of $^3$H-thymidine incorporation (FIGS. 4A, 4B and 4C, respectively) and IL-2 production (FIG. 4D) in the Anx-A1 deficient T cells compared to control unstimulated T cells.

Example 3

Activation of AP-1, NF-κB and NFAT in Presence or Absence of Anx-A1

Investigations were carried out into how exogenous and endogenous Anx-A1 modulates T cell activation. The three major transcriptional activators of T cells, namely Activator Protein-1 (AP-1), Nuclear Factor-κB (NF-κB) and Nuclear Factor of Activated T cells (NFAT) were analysed in cells stimulated in presence of hrAnx-A1.

Figure 5:
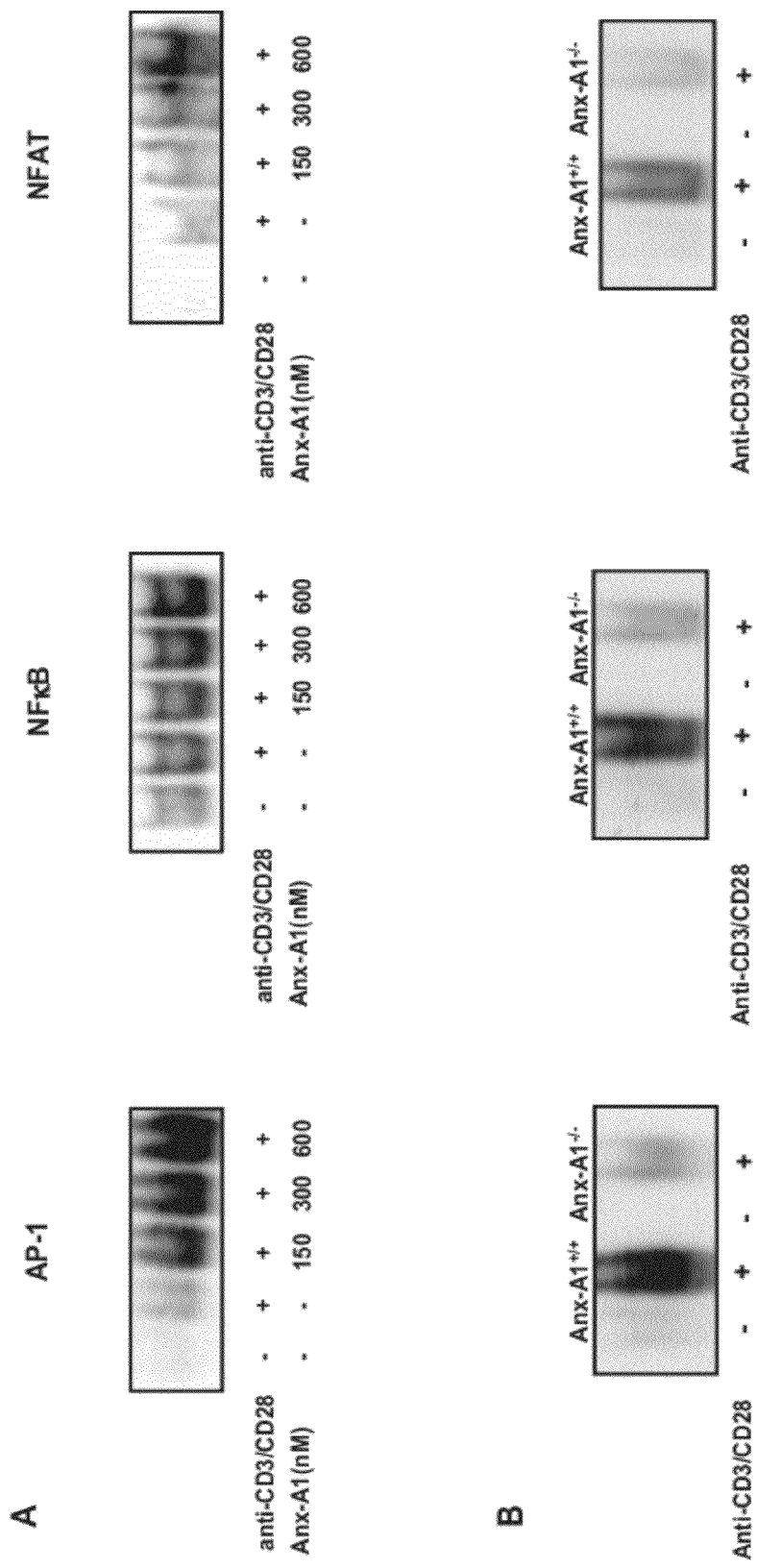
FIG. 5 shows activation of Activator Protein-1 (AP-1), Nuclear Factor-κB (NF-κB) and Nuclear Factor of Activated T cells (NFAT) in the presence or absence of Anx-A1 (FIG. 5A), and a comparison of the activation of AP-1, NF-κB and NFAT in Anx-A1$^{+/+}$ and Anx$^{-/-}$ T cells (FIG. 5B).

FIG. 5A is an Electrophoretic Mobility Shift Assay for AP-1, NF-κB and NFAT activation in T cells stimulated with anti-CD3/CD28 (1.25 µg/ml) in presence or absence of the indicated concentration of hrAnx-A1. FIG. 5B shows a comparison of the activation of AP-1, NF-κB and NFAT in Anx-A1$^{+/+}$ and Anx$^{-/-}$ T cells stimulated with anti-CD3/CD28 (5.0 µg/ml).

The results demonstrated increased activation of all three transcription factors (FIG. 5A). Conversely, Anx-A1$^{-/-}$ T cells showed a decreased activation of these transcription factors compared to their control littermates (FIG. 5B).

Example 4

Externalization of FPRL-1 and Anx-A1 in T Cells

We investigated whether T cells express the receptor for Anx-A1, the Formyl Peptide Receptor Like-1 (FPRL-1). FACS staining of unstimulated human Peripheral Blood T (PBT) cells with specific monoclonal anti-FPRL-1 antibody demonstrated no receptor expression. However, stimulation with anti-CD3/CD28 induced the externalization of FPRL-1 within 1 hour followed by a stable steady state expression on the cell surface (FIG. 6A). Interestingly, a similar pattern was observed for Anx-A1. Thus, analysis of Anx-A1 distribution in human PBT demonstrated that the protein is evenly distributed between the cytosol and membrane. However, when cells were stimulated with anti-CD3/CD28, accumulation of Anx-A1 at the membrane was observed.

The protein is then exported to the outer side of the membrane and released into the extracellular milieu. Consistent with this model, when we immunoprecipitated Anx-A1 from the culture supernatant of human PBT stimulated with anti-CD3/CD28, we observed an increased release of Anx-A1 compared to control unstimulated cells (FIG. 6B). Collectively, these observations demonstrate that signalling through the TCR increases Anx-A1 release, concomitant with the upregulation of its receptors.

In physiological conditions, the Anx-A1/FPRL-1 integrates with the TCR to modulate the strength of TCR signalling. However, in pathological conditions, such as in RA or systemic lupus erythematosus (unpublished data), where the protein is expressed at higher levels this could lead to increased T cell activation due to lower threshold of TCR signalling (FIG. 6C).

Example 5

Exogenous and Endogenous Anx-A1 Modulates Th1/Th2 Differentiation

Recent studies have postulated that the strength of TCR signalling influences T cell lineage commitment to Th1 or Th2 effector cells. Given the increased or decreased TCR signalling in T cells treated with hrAnx-A1 (FIGS. 3 and 5A) or Anx-A1$^{-/-}$ cells (FIGS. 4 and 5B), we then sought to determine whether different levels of Anx-A1 would influence T cell differentiation into Th1 or Th2 cells.

Naïve lymph node T cells were differentiated in vitro in Th1 (black bars) or Th2 (white bars) conditions in presence or absence of hrAnx-A1 (600 nM) and then restimulated with plate-bound anti-CD3 (5.0 µg/ml) for 8 h to measure Th1 or Th2 cytokine production. The results are shown in FIG. 7A. Values are mean±S.E. of n=4-5 mice. **$P<0.01$ As shown in FIG. 7A, differentiation of naïve T cells (CD44lo, CD62Lhi) in Th1 (anti-CD3/CD28, IL2, IL12 and anti-IL4) or Th2 (anti-CD3/CD28, IL2, IL4 and anti-IFNγ) conditions in the presence of hrAnx-A1 increased IL2 and IFNγ production with a concomitant decrease of IL4 and IL 10 release upon anti-CD3 re-stimulation.

Naïve lymph node T cells from Anx-A1$^{+/+}$ or Anx-A1$^{-/-}$ mice were differentiated in vitro in Th1 (first and second graphs from the left) or Th2 (third and fourth graphs from the left) conditions and then restimulated with plate-bound anti-CD3 (5.0 µg/ml) for 8 h to measure Th1 or Th2 cytokine production. The results are shown in FIG. 7B. Values are mean±S.E. of n=4-5 mice. **$P<0.01$ As shown in FIG. 7B, similar findings were also obtained with respect to the endogenous protein: analysis of Th1/Th2 cytokine production in differentiated Th1/Th2 cells from Anx-A1$^{+/+}$ or Anx-A1$^{-/-}$ mice yielded higher levels of IL2 and IFNγ in wild-type mice compared with knockout mice, with opposite profiles for IL4 and IL13 production.

Example 6

Anx-A1 and Rheumatoid Arthritis

To prove that hrAnx-A1 increased T cell activation in vivo, we used a mouse model of chronic autoimmune disease, the collagen-induced arthritis (CIA) model in DBA mice. Mice were injected with hrAnx-A1 daily for 12 days after immunization with collagen (time during which naïve cells differentiate in Th effector cells) and thereafter the progression of the disease upon antigen challenge was analyzed. FIG. 8 shows paw volume (FIG. 8A) and clinical score (FIG. 8B) of the mice treated with PBS (100 µl) or hrAnx-A1 (1 µg s.c. twice a day). Synchronization of disease onset was obtained by boosting with collagen on day 21, and clinical signs were evident from day 22 (day 1 of the onset of the diseases). Values are mean±S.E. of n=6-8 mice. Groups were compared using the Maim-Whitney test. *$P<0.01$ As can be seen from FIGS. 8A and 8B, treatment of mice with hrAnx-A1 exacerbated the signs and symptoms of arthritis compared to mice treated with PBS vehicle, confirming that high levels of Anx-A1 influence T cell activation and differentiation and that these effects influence the disease development in a mouse model of RA.

To investigate the clinical relevance of these studies Anx-A1 expression was analyzed in CD4+ peripheral T cells and synovial CD3+ cells from RA patients. FIG. 8C shows the results. The median values are indicated by horizontal lines and p values of the Maim-Whitney test are shown. *$P<0.01$.

As shown in FIG. 8C, RA CD4+ cells express high levels of Anx-A1 mRNA and protein (data not shown) compared with cells from healthy control volunteers (HC).

Fluorescence immunohistochemistry was also carried out using green and red fluorescent tagged secondary antiserum, as shown in each panel of FIG. 8D. This immunohistochemical analysis of Anx-A1 expression in the synovial tissue of RA patients revealed a high degree of colocalization with CD3+ cells. Therefore, considering that CD4 cells from RA patients express higher levels of Anx-A1, it can be concluded that the dysregulated expression of this protein might contribute to the development of this disease.

Example 7

Effects of Full Length hrAnx-A1 and the N-terminal Peptide Ac 2-26 on T Cell Activation The effects of an N-terminal peptide of hrAnx-A1 (peptide Ac 2-26) and of full length hrAnx-A1 on T cell activation were investigated. IL-2 production from murine naïve lymph node T cells was stimulated with 0.6, 1.25 or 2.5 µg/ml of anti-CD3/CD28 in the presence or absence of full length hrAnx-A1 (300 nM) or the Anx-A1 derived N-terminal peptide Ac.2-26 (100 µM) for 24 hrs.

It was found that the N-terminal peptide Ac.2-26 retains most of the biological activity of the full-length protein, i.e. increased IL-2 production (FIG. 9) and T cell proliferation (data not shown).

Example 8

Anx-A1 and Atherosclerosis

To investigate if Anx-A1 is expressed in human atherosclerotic plaques, sections of carotid atherosclerotic plaques removed from patients during carotid endarteretomy surgery were stained with a mouse monoclonal anti human Anx-A1 antibody (mAb1B). The production of this antibody is described in Pepinsky et al FEBS Letters 261: 247-252, 1990. Briefly, BALB/c mice were immunized with an intraperitoneal injection of annexin-1 (referred to as lipocortin-1 in Pepinsky et al) in complete Freund's adjuvant. The animals were boosted on days 14 and 28 with annexin-1 in incomplete Freund's adjuvant. After 6 weeks, test bleeds were taken and screened for antibodies that blocked annexin-1 activity. Spleen cells from mice whose antisera displayed anti-annexin activity were fused with SP3×Ag8 cells for hybridoma production. Hybridoma culture supernatants were assayed for antibodies that could precipitate radiolabeled annexin-1, and hybridomas producing antibodies that precipitated over 50% of the input counts were subcloned by limiting dilution. The most promising lines were grown as ascites in pristane-primed mice and the monoclonal antibodies were affinity-purified on protein A sepharose, using the Pierce binding and elution buffer systems.

As shown in FIG. 10, a compact and clear staining for Anx-A1 could be observed within the plaque confirming that the inflammatory infiltrate within these tissues expresses high levels of Anx-A1.

Similar analysis was also carried out in ApoE$^{-/-}$ mice. Localization of Anx-A1 in the aortic sinus and the brachiocefalic artery (BCA) of 10 month old ApoE$^{-/-}$ mice were performed by confocal microscopy to determine the expression and spatial distribution of Anx-A1. Non atherosclerotic arterial tissue lacked immunoreactive Anx-A1 (data not shown). In contrast, atherosclerotic plaque from both aortic sinus and BCA stain strongly for Anx-A1 (FIG. 11).

A clear immunoreactivity for Anx-A1 was detected in proximity of the fibrous cap in both aortic sinus (FIG. 11A) and BCA (FIG. 11B) and in proximity of the necrotic core of the plaque in the aortic sinus (FIG. 11B). These results demonstrate that Anx-A1 is expressed in both human and murine atherosclerotic plaques and suggest that its expression could potentially influence plaque stability.

Example 9

Anx-A1 and Systemic Lupus Erythematosus (SLE)

Clinical studies on the biological functions of Annexin-1 have associated the presence of autoantibodies against this protein with the development of autoimmune diseases including systemic lupus erythemathosus (SLE), rheumatoid arthritis and inflammatory bowel disease. In light of these findings we hypothesized that the generation of these autoantibodies might be due to an uncontrolled expression of Annexin-1 in these patients. To verify this hypothesis, the expression level of Annexin-1 in T cells collected from healthy volunteers and SLE patients was analyzed. Annexin-1 mRNA and protein were expressed at a much more marked level in the SLE T cells (FIG. 12). Thus, these results support the hypothesis that increased Annexin-1 expression in SLE T cells, and therefore in T cells from patients with other autoimmune pathologies, might be responsible for the increased levels of Th1 cytokines described in these pathologies, thereby representing a risk factor for the development of autoimmune diseases.

Example 10

Inhibition of T Cell Activation by Anti-Anx-A1 Antibodies

Purified human peripheral blood T cells were incubated with a mixture of anti-CD3 and anti-CD28 antibodies (5 μg/ml) to activate the T cell receptor (TCR): this occurred as demonstrated in FIG. 13 by the remarkable production of interleukin-2 (IL-2), a cytokine central to T cell activation and differentiation.

Cells were then incubated with different concentrations (1.0, 0.1, 0.01 and 0.001 micrograms/ml) of a neutralising mouse monoclonal antibody raised against human recombinant annexin 1 (mAb1A). The production of this antibody is described in Pepinsky et al FEBS Letters 261: 247-252, 1990 and in Example 8.

Treatment with mAb1A produced a concentration dependent inhibition of IL-2 production (FIG. 13) and cell proliferation (data not shown). IgG was used as a control at concentrations of 1.0, 0.1, 0.01 and 0.001 micrograms/ml and was without efficacy at all concentrations. The results showed that blockade of annexin-1 effects seemed to be more effective at lower concentrations of the specific monoclonal antibody mAb1A.

In all cases, data are mean±SE of triplicate measurements. *P<0.01.

Purified human peripheral blood T cells from a different donor were then incubated with a mixture of anti-CD3 and anti-CD28 antibodies at a different concentration (1 μg/ml) to activate the T cell receptor (TCR). Again, this occurred as demonstrated in FIG. 14 by the production of interleukin-2 (IL-2), but at a lower level due to the lower concentration of anti-CD3 and anti-CD28 antibodies used.

Again, cells were then incubated with different concentrations (1.0, 0.1, 0.01 and 0.001 micrograms/ml) of the neutralising mouse monoclonal antibody raised against human recombinant annexin 1 (mAb1A). Treatment with mAb1A produced a concentration dependent inhibition of IL-2 production (FIG. 14). IgG was used as a control at a concentration of 1.0 micrograms/ml and was without efficacy. Again, the results showed that blockade of annexin-1 effects seemed to be more effective at lower concentrations of the specific monoclonal antibody mAb1A, except with a concentration of 1.0 micrograms/ml of mAb1A.

In all cases, data are mean±SE of triplicate measurements. *P<0.01.

These experiments demonstrate that endogenous annexin 1 promotes T cell activation in the presence of a specific stimulus. In addition, blockade of the annexin 1 pathway attenuated T cell activation by up to 50%. The fact that inhibition reached a maximum of around 50% suggests that "normal and housekeeping" immunity would not be affected by treatment of T cell-mediated diseases using a molecule which specifically binds to Anx-A1, as claimed.

Example 11

Anx-A1 and Multiple Sclerosis (MS)

Materials and Methods
Reagents
The Myelin Oligodendrocyte Glycoprotein peptide (MOG)$_{33-55}$ (MEVGWYRSPFSRVVHLYRNGK) (SEQ ID NO: 22) was synthesized and purified by Cambridge Research Biochemicals (Billingham, UK). Complete Freund's adjuvant containing *Mycobacterium tuberculosis* H37a was purchased from Difco while *Bordetella pertussis* toxin was from Sigma-Aldrich Co (Poole, UK). Unless otherwise specified, all the other reagents were from Sigma-Aldrich Co.
Mice
Male AnxA1 null mice were as previously described (Hannon et al., Faseb J, 17: 253-255, 2003; Roviezzo et al., J. Physiol Pharmacol 53: 541-553, 2002) (9-11 week old) and were backcrossed on a C57BL/6 background for >10 generations and bred at B&K animal care facilities (Hull, UK). Age and gender-matched control C57BL/6 mice were used as control for all experiments. Animals were kept under standard conditions and maintained in a 12 h/12 h light/dark cycle at 22±1° C. in accordance with United Kingdom Home Office regulations (Animal Act 1986) and of the European Union directives.
Induction of EAE
Mice were immunized subcutaneously on day 0 with 300 μl of emulsion consisting of 300 μg of MOG$_{35-55}$ in PBS combined with an equal volume of CFA containing 300 μg heat-killed *M. tuberculosis* H37Ra. The emulsion was injected in both flanks and followed by an intraperitoneal injection of *B. pertussis* toxin (500 ng/100 μl) in 100 μl of saline on days 0 and 2. Mice were observed daily for signs of EAE and weight loss. Disease severity was scored on a 6-point scale: 0=no disease; 1=partial flaccid tail; 2=complete flaccid tail; 3=hind limb hypotonia; 4=partial hind limb paralysis; 5=complete hind limb paralysis; 6=moribund or dead animal.
Cell Proliferation Assay
Lymph node cells ($10^5$ cells/200 μl) obtained from mice immunized with MOG$_{33-55}$ for 14 days were stimulated with MOG$_{33-55}$ (50-100 μg/200 μl) for 48 h in 96 well plates. During the last 12 h, cultures were pulsed with 1 μCi of [$^3$H]-thymidine (Amersham Pharmacia Biotech, Buckinghamshire, UK) and incorporated radioactivity was measured by automated scintillation counter (Packard Instrument Company, Inc., Ill., US).
Cytokine ELISA
Lymph node cells ($10^6$ cells/ml) obtained from mice immunized with MOG$_{33-55}$ for 14 days were stimulated with MOG$_{33-55}$ (100 μg/ml) for 4 days. Cell supernatants were collected and analyzed for IFN-γ, IL-2, IL-17A and TNF-α content using ELISA kits (eBioscience, Dorset, UK) according to manufacturer's instructions.

Isolation of Inflammatory Cell from the Spinal Cord

Mice were killed using $CO_2$. The spinal cords were expelled from the spinal column with PBS by hydrostatic pressure using a syringe attached to a 21-gauge needle. Tissues were cut in small pieces and passed through cell strainer (70 nm; BD Falcon) using the plunger of a sterile 1 ml syringe. The single cell suspension was centrifuged for 10 min at 390×g, resuspended in 20 ml of PBS containing 30% of Percoll (Sigma) and overlayed onto 10 ml of PBS containing 70% Percoll. After centrifugation at 390×g for 20 min, the mononuclear cells were removed from the interphase, washed, and resuspended in FACS buffer (PBS containing 1% FCS and 0.02% $NaN_3$) for further analysis.

Flow Cytometry

Cell samples from Percoll-purified spinal cord tissues or Ficoll-purified lymph nodes were resuspended in FACS buffer containing CD16/CD32 FcγIIR blocking antibody (clone 93; eBioscience) for 30 min at 4° C. Thereafter, cell suspensions were labelled with the FITC-conjugated anti-CD3 (1:100; clone 145 2C11) or anti-F4/80 (1:100; clone BMT) while lymph node cells were stained with anti-CD4-FITC (1:500; clone L3T4) and anti-CD8 (1:1000; clone Ly-2) for 30 min at 4° C., prior to analysis by FACS calibur using CellQuest software (Becton Dickinson). At least $10^4$ cells were analyzed per sample, and determination of positive and negative populations was performed based on the staining attained with irrelevant IgG isotypes.

Histology

Spinal cord tissues were dissected and fixed in 4% neutral buffered formalin for 48 hrs and then incubated with decalcifying solution containing EDTA (0.1 mM in PBS) for 14 days prior to paraffin embedding. Histological evaluation was performed on paraffin-embedded sections sampled at various time points depending on disease severity. Spinal cord sections (5 μm) were deparaffinized with xylene and stained with haematoxylin and eosin (H&E) to assess inflammation. The staining for AnxA1 was performed on frozen sections using anti-AnxA1 (dilution 1:500; Zymed, Invitrogen) and anti-rabbit Ig horseradish peroxidase (HRP)-conjugated antibodies (dilution 1:500; Dako). Double staining for AnxA1 and CD3 or F4/80 was carried out as previously described using FITC-conjugated anti-CD3 (1:100; clone 145 2C11) or anti-F4/80 (1:100; clone BMT). Sections were also counterstained with haematoxylin. In all cases, a minimum ≥3 sections per animal were evaluated. Phase-contrast digital images were taken using the Image Pro image analysis software package.

Statistical Analysis

Prism software (GraphPad software) was used to run all the tests. Statistical evaluations of cell frequency, proliferation and cytokine production were performed using two-tailed, unpaired Student's t tests. ANOVA were applied to analyze the EAE clinical grading. A p value of <0.05 was considered to be statistically significant. P-values lower than 0.05 were considered significant. Data are presented as mean±S.E.M of n samples per group.

Results

AnxA1 Expression Correlates with the Severity of Experimental Autoimmune Encephalomyelitis (EAE)

The correlation between AnxA1 levels in the spinal cord content and extent of infiltrating mononuclear cells in the CNS were assessed in a mouse model of MS induced by immunization with $MOG_{35-55}$, EAE. $MOG_{35-55}$-induced EAE is a model for autoimmune demyelination of the CNS and has been widely used to investigate pathogenic mechanisms responsible for the development of MS. To this aim, spinal cords and brains of wild type mice immunized with $MOG_{35-55}$ peptide at different stages of the diseases i.e. at day 12 (score 0), day 18 (score 2) and day 20 (score 4) were collected and immunohistochemistry for AnxA1 was performed side by side with hematoxylin and eosin staining.

As shown in FIG. 15, spinal cord tissues collected during the induction phase of mice with no signs of disease showed a faint staining for AnxA1 (score 0, FIGS. 15A and B, respectively). However, with the onset of clinical signs and the appearance of inflammatory infiltrates in the CNS, discrete patches of AnxA1 immunostaining were observed all around the meninges (score 2, FIGS. 15A and B, respectively). As the disease progressed, an increase in number of AnxA1-positive cellular infiltrate patches was observed (score 4, FIGS. 15A and B, respectively), suggesting that the infiltration of inflammatory cells expressing high levels of AnxA1 is correlated with the severity of the disease.

To identify the cellular sources of AnxA1 immunoreactivity in the spinal cord, double immunofluorescence staining of the sections was performed with anti-AnxA1 and either anti-CD3 (marker for T cells) or anti-F4/80 (marker for macrophages). A large number of infiltrated T cells and macrophages was detected in the spinal cord sections of mice at the peak of EAE (FIGS. 16A and B, middle panels, respectively). However, AnxA1 staining in the same sections showed a partial co-localization with both T cells and macrophages without particular preference for one or the other cell types (FIGS. 16A and B, right panels, respectively).

$AnxA1^{-/-}$ Mice Develop an Impaired EAE

Since AnxA1 expression was upregulated at the peak of EAE, the role of this protein on the development of EAE was investigated. $AnxA1^{+/+}$ and $AnxA1^{-/-}$ mice were immunized s.c. with $MOG_{35-55}$ peptide in CFA on day 0, and then injected i.v. with *B. pertussis* toxin on both day 0 and day 2. Both $AnxA1^{+/+}$ and $AnxA1^{-/-}$ mice started to develop EAE from day 12 after immunization, reaching peak disease around day 20. However, $AnxA1^{-/-}$ mice had reduced levels of disease compared to $AnxA1^{+/+}$ (FIG. 17A). Interestingly, this was evident and significant only at the later stage of the disease i.e. from day 18 to 23 and onwards.

Studies on animal models of EAE have demonstrated that the acute phase of the disease coincides with weight loss, probably due to anorexia and deficient fluid uptake. Weight measurement of immunized mice correlated with the severity of the clinical score and showed a reduced weight loss—from day 18 onwards—in the $AnxA1^{-/-}$ mice compared to $AnxA1^{+/+}$ controls (FIG. 17B). Further comparison of development of EAE in $AnxA1^{+/+}$ and $AnxA1^{-/-}$ mice showed a decrease in both the mortality rate and maximum disease score, without differences in the incidence rate or disease onset (Table 1).

TABLE 1

Clinical parameters of $MOG_{35-55}$-induced EAE in $AnxA1^{+/+}$ and $AnxA1^{-/-}$ mice (mean ± SEM, n = 10/group)

| Mice | Incidence§ | Mortality | Onset day (mean ± SEM) | Max. score (mean ± SEM) |
|---|---|---|---|---|
| $AnxA1^{+/+}$ | 100% (10/10) | 33.3% (3/10) | 16.4 ± 2.3 | 5.7 ± 0.2 |
| $AnxA1^{-/-}$ | 100% (10/10) | 0% (0/10)** | 15.9 ± 1.3 | 4.3 ± 0.1** |

**p < 0.01, representative of 3 experiments § EAE clinical score equal or greater than 1.

In Vitro Recall Response to MOG$_{35-55}$ in Anx1$^{-/-}$ Mice

T cells play a key role in the development of EAE and AnxA1$^{-/-}$ T cells have an impaired capacity to respond to anti-CD3/CD28 stimulation. In light of these findings, it was investigated whether the decreased development of EAE in AnxA1$^{-/-}$ mice was associated with a lower response to antigen-stimulation. Lymph node cells from AnxA1$^{+/+}$ and AnxA1$^{-/-}$ mice, collected 14 days after immunization, were stimulated in vitro with MOG$_{35-55}$. AnxA1 lymph node cells showed a decreased rate of proliferation and produced lower levels of IL-2 when stimulated with MOG$_{35-55}$ compared to wild-type mice (FIGS. 18A and B, respectively). Similar results were obtained with splenocytes (data not shown).

These results on cell proliferation were mirrored in the number of cells recovered from the spleen and the draining lymph nodes of the immunized mice. The total cell count of Ficoll-purified spleen and lymph node mononuclear cells from the same animals, revealed a significant decrease in AnxA1$^{-/-}$ mice compared to controls (FIGS. 19A and B, respectively), with no measurable changes in the percentages of CD4 or CD8 positive cells (FIGS. 19C and D, respectively).

Reduced MOG$_{35-55}$-Specific Th1 and Th17 Cytokine Responses in AnxA1$^{-/-}$ Mice Studies using draining lymph node cells from MOG$_{35-55}$ immunized C57/BL6 mice showed significant changes in Th1 and Th17 cytokine production. Analysis of cytokine production from AnxA1$^{-/-}$ lymph node cells upon re-challenge with MOG$_{35-55}$ for 96 h showed a decreased production of Th1 cytokines IFN-γ, IL-2, and TNF-α compared to wild type cells (FIGS. 20A-C). Similarly, measurement of Th17 signature product IL-17, revealed decreased levels of this cytokine in AnxA1$^{-/-}$ compared to wild type (FIG. 20D).

T Cell Infiltration in the Nervous System of AnxA1$^{-/-}$ Mice During EAE

The reduced signs of EAE in AnxA1$^{-/-}$ mice from day 18 onwards, prompted us to investigate whether there could be a neuro-pathological correlate. The spinal cords of AnxA1$^{+/+}$ and AnxA1$^{-/-}$ treated mice, collected at day 18 or 22, were analyzed for histological evidence of inflammation. It was found that there were reduced numbers of immune cell infiltrates detected in AnxA1$^{-/-}$ mice compared to AnxA1$^{+/+}$ animals. (FIGS. 21A and B).

The reduced histological signs of inflammation in AnxA1$^{-/-}$ mice were associated with a reduced number of CD3 and F4/80 positive cells infiltrating the CNS (FIGS. 21C and D, respectively). These qualitative analyses were confirmed by FACS measuring the percentages of CD3 and F4/80 positive leucocytes isolated from day 18 spinal cord tissues. Consistent with the immunohistochemistry results, AnxA1$^{-/-}$ mice had about 60 and 80% less T cells and macrophages, respectively, compared to AnxA1$^{-/-}$ mice (FIGS. 22A and B, respectively).

The results show that there is a remarkable accumulation of Annexin-1 expressing cells in the spinal cord of mice at the peak of the disease. There is therefore a correlation between Annexin-1 expression and the development of EAE.

In addition, the results show that Annexin-1 deficient mice develop less severe EAE. Ablating Annexin-1 expression therefore limits the development of EAE, a mouse model for MS.

The invention claimed is:

1. A method of treating a T cell-mediated disease in a human comprising systemically administering to the human in need thereof a therapeutically effective amount of an antibody, or fragment thereof, that binds to Annexin-1 (Anx-A1), wherein the T cell-mediated disease is rheumatoid arthritis or multiple sclerosis, and wherein the antibody, or fragment thereof, ameliorates, eliminates or prevents one or more symptoms of the T cell-mediated disease.

2. The method of claim 1 wherein the antibody binds to an N-terminal peptide of Anx-A1 of at least 50 amino acid residues.

3. The method of claim 1 wherein the antibody binds to SEQ ID NO:1.

4. The method of claim 1 wherein the antibody binds to a fragment of at least 6 amino acids of SEQ ID NO:1.

5. The method of claim 1 wherein the antibody is a monoclonal antibody.

6. The method of claim 1 wherein the antibody fragment is chosen from Fab fragment, F(ab')$_2$ fragment, Fv fragment, and single chain Fv (scFv) molecule.

7. The method of claim 1 wherein the antibody is a chimeric antibody.

8. The method of claim 1 wherein the antibody is a humanized antibody.

9. The method of claim 1 wherein the T cell-mediated disease is rheumatoid arthritis.

10. The method of claim 1 wherein the T cell-mediated disease is multiple sclerosis.

* * * * *